(12) United States Patent
Lugmair et al.

(10) Patent No.: US 7,503,515 B2
(45) Date of Patent: *Mar. 17, 2009

(54) METHODS AND APPARATUS FOR MECHANICAL TREATMENT OF MATERIALS SUCH AS CATALYSTS

(75) Inventors: Claus G. Lugmair, San Jose, CA (US); Alfred Hagemeyer, Rheine (DE); Lynn Van Erden, Livermore, CA (US); Anthony F. Volpe, Jr., Santa Clara, CA (US); David M. Lowe, Sunnyvale, CA (US); Yumin Liu, Menlo Park, CA (US)

(73) Assignee: Symyx Technologies, Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/519,358

(22) Filed: Sep. 11, 2006

(65) Prior Publication Data

US 2007/0007372 A1  Jan. 11, 2007

Related U.S. Application Data

(62) Division of application No. 10/880,412, filed on Jun. 28, 2004, now Pat. No. 7,111,802, which is a division of application No. 09/902,552, filed on Jul. 9, 2001, now Pat. No. 6,755,364.

(60) Provisional application No. 60/216,777, filed on Jul. 7, 2000.

(51) Int. Cl.
*B02C 17/18* (2006.01)

(52) U.S. Cl. .................. 241/79; 241/137; 241/179

(58) Field of Classification Search .............. 241/137, 241/171, 172, 79, 179

See application file for complete search history.

(56) References Cited

U.S. PATENT DOCUMENTS

| 921,248 A | 5/1909 | Honeywood |
| 1,121,118 A | 12/1914 | Moyle |
| 1,627,488 A * | 5/1927 | Crowe .................. 241/44 |

(Continued)

FOREIGN PATENT DOCUMENTS

DE        196 32 779 A1    2/1996

(Continued)

OTHER PUBLICATIONS

Office Action dated Oct. 24, 2007 for related U.S. Appl. No. 11/845,937, 9 pgs.

(Continued)

*Primary Examiner*—Mark Rosenbaum
(74) *Attorney, Agent, or Firm*—Senniger Powers LLP

(57) ABSTRACT

Methods and apparatus for combinatorial (i.e., high-throughput) materials research, such as catalysis research, that involves parallel apparatus for simultaneously effecting mechanical treatments such as grinding, mixing, pressing, crushing, sieving, and/or fractionating of such materials are disclosed. The methods and apparatus are useful for mechanically treating catalysis materials and other solid materials, including without limitation, electronic materials such as phosphors, colorants such as pigments, and pharmaceuticals such as crystalline drugs or drug candidates. The simultaneous protocols and parallel apparatus offer substantial improvements in overall throughput for preparing arrays of materials, such as catalysis materials.

12 Claims, 9 Drawing Sheets

U.S. PATENT DOCUMENTS

| | | | |
|---|---|---|---|
| 1,794,041 A * | 2/1931 | Stone | 241/75 |
| 2,884,209 A * | 4/1959 | Bargero | 241/153 |
| 3,319,792 A | 5/1967 | Leder | |
| 3,830,437 A * | 8/1974 | Everett | 241/137 |
| 4,233,190 A | 11/1980 | Schaefer | |
| 4,467,046 A | 8/1984 | Smith et al. | |
| 4,665,042 A | 5/1987 | Budge et al. | |
| 4,802,836 A | 2/1989 | Whissell | |
| 5,135,903 A | 8/1992 | Birkenstock et al. | |
| 5,424,262 A | 6/1995 | de Lasa et al. | |
| 5,513,806 A * | 5/1996 | Falcon-Steward | 241/21 |
| 5,641,395 A | 6/1997 | Hettinger, Jr. et al. | |
| 5,733,839 A | 3/1998 | Espinoza et al. | |
| 5,776,359 A | 7/1998 | Schultz et al. | |
| 5,958,714 A | 9/1999 | Gordon | |
| 5,959,297 A | 9/1999 | Weinberg et al. | |
| 5,985,356 A | 11/1999 | Schultz et al. | |
| 6,004,617 A | 12/1999 | Schultz et al. | |
| 6,030,917 A | 2/2000 | Weinberg et al. | |
| 6,063,282 A | 5/2000 | Moulton | |
| 6,063,633 A | 5/2000 | Willson, III | |
| 6,063,724 A | 5/2000 | Resasco et al. | |
| 6,087,181 A | 7/2000 | Cong | |
| 6,149,882 A | 11/2000 | Guan et al. | |
| 6,175,409 B1 | 1/2001 | Nielsen et al. | |
| 6,451,261 B1 | 9/2002 | Bodner | |
| 6,511,617 B1 | 1/2003 | Martin et al. | |
| 6,602,714 B1 | 8/2003 | Tagge et al. | |
| 6,627,445 B1 | 9/2003 | Akporiaye et al. | |
| 6,852,289 B2 | 2/2005 | Gordon | |
| 7,111,802 B2 * | 9/2006 | Lugmair et al. | 241/79 |
| 7,147,109 B2 | 12/2006 | Stichert | |

FOREIGN PATENT DOCUMENTS

| | | |
|---|---|---|
| DE | 198 09 477 A1 | 9/1999 |
| WO | WO 98/03521 A1 | 1/1998 |
| WO | WO 99/19724 A1 | 10/1998 |
| WO | WO 00/09255 A2 | 2/2000 |
| WO | WO 00/14529 A1 | 3/2000 |
| WO | WO 00/17413 A2 | 3/2000 |
| WO | WO 00/51720 A2 | 9/2000 |
| WO | WO 01/66245 A2 | 9/2001 |

OTHER PUBLICATIONS

Office Action dated Mar. 28, 2008 for related U.S. Appl. No. 11/845,937, 18 pgs.

Fayed et al., Ed., Handbook of Powder Science & Technology, 2nd Ed. (Chapman & Hall, New York, NY, 1997).

Obenauf et al., Ed., SPEX "CertiPrep Handbook of Sample Preparation and Handling", SPEX CERTIPREP, 1999 6 pages.

Obenauf et al., Catalog of SPEX CertiPrep, Inc. (Metuchen, NJ) pp. 28-39, 90-91, 104-105, and 114-119 (1999).

Senkan, S. et al., "High-Throughput Testing of Heterogeneous Catalyst Libraries Using Array Microreactors and Mass Spectrometry," Angew. Chem. Intl. Ed., vol. 38, No. 18, pp. 2794-2799 (1998).

Van Giezen, J.C., "The Catalytic Combustion of Methane," Thesis, pp. 34-35 (1997).

Wijngaarden et al., "Industrial Catalysis—Optimizing Catalysts and Processes," Wiley-VCH, Germany (1998).

Dautzenberg, F.M., "Quality Principles for Catalysts Testing During Process Development," Proceedings of the Nato Advanced Study Institute on Combinatorial Catalysts and High Throughput Catalvst Design and Testing. Jul. 11-24, 1999. Vilamoura. Portugal. vol. 560. pp. 67-69 (2000).

Hendrix, Charles D., "What Every Technologist Should KNow About Experimental Design," Chemtech, vol. 9, pp. 167-174, Mar. 1979.

Perez-Ramirez, J. et al., "The Six-Flow Reactor Technology: A Review on Fast Catalyst Screening and Kinetic Studies," Catalysis Today, vol. 60, pp. 93-109, Jul. 10, 2000.

Calleja et al., "Co/HZSM-5 Catalyst For Syngas Conversion: Influence of Process Variables," Fuel, vol. 74 No. 3. pp. 445-451 (1995).

* cited by examiner

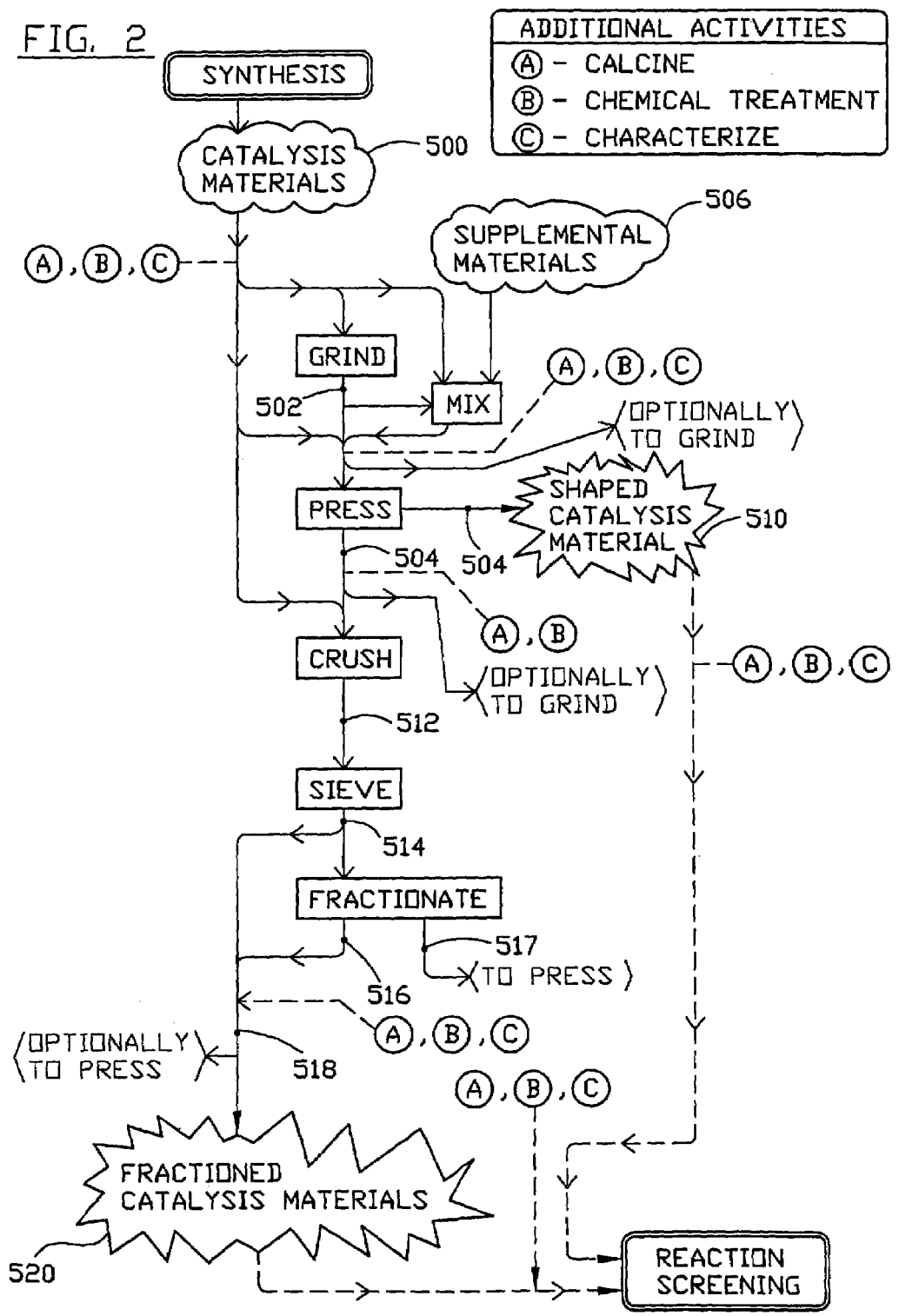

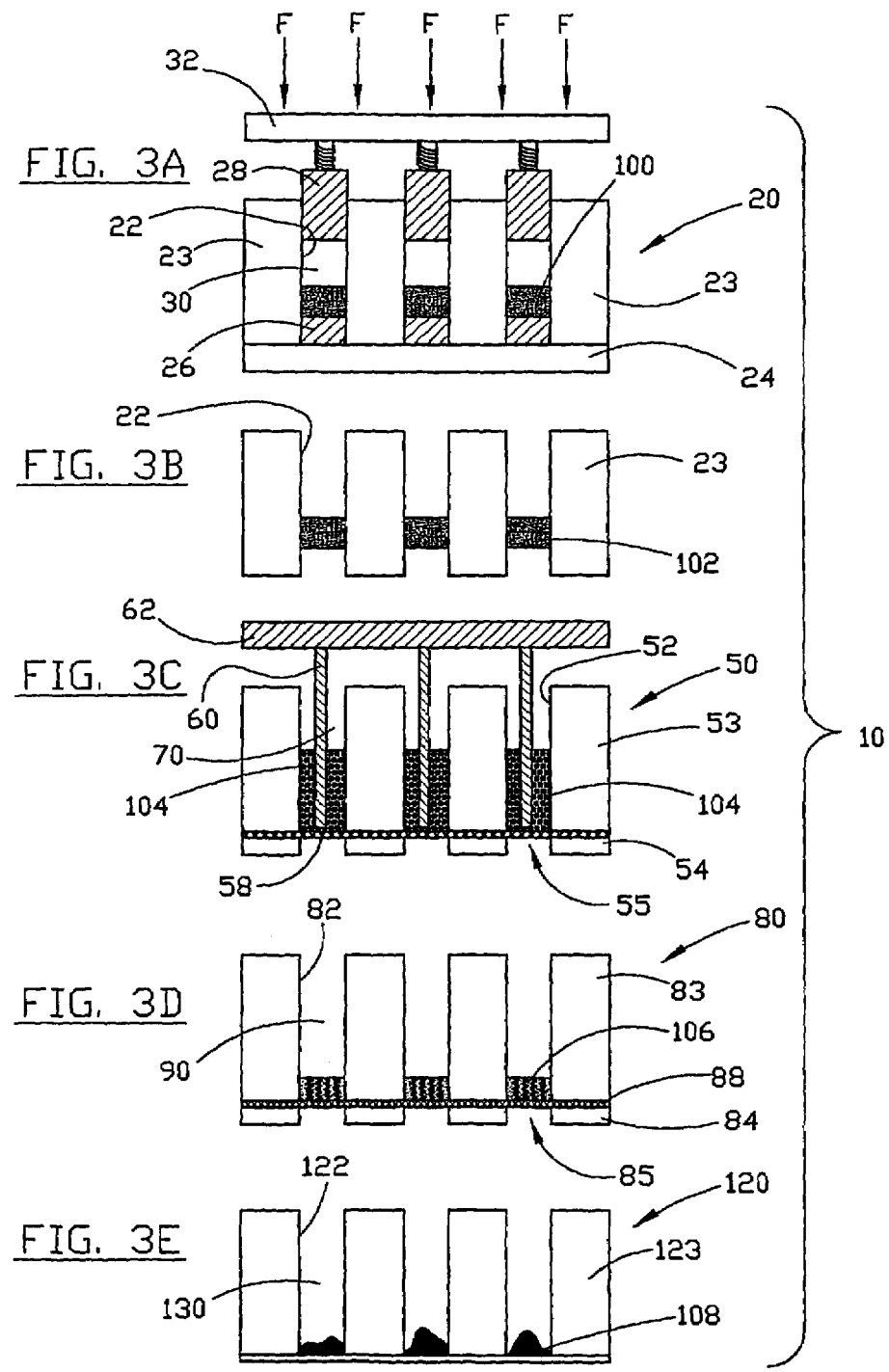

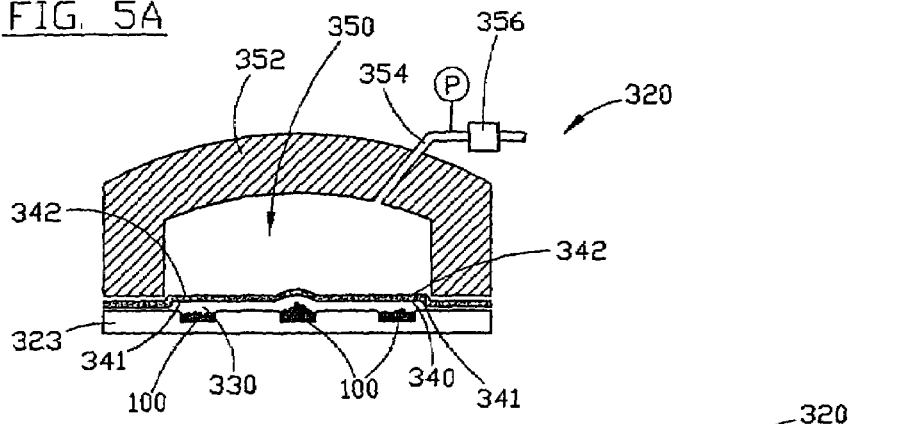
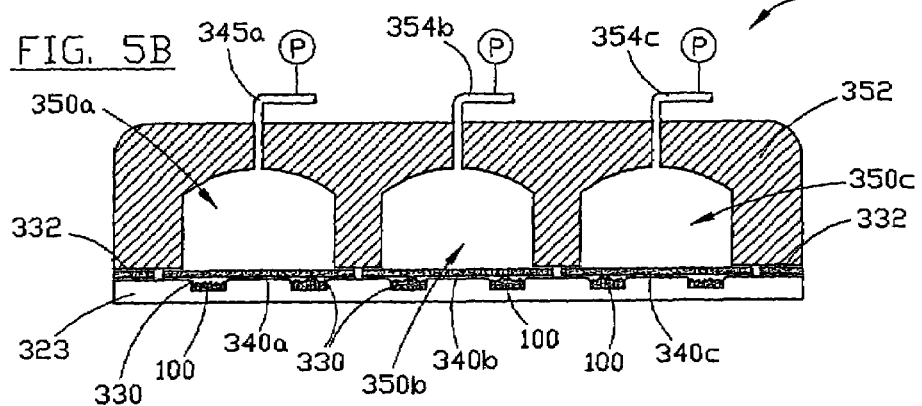
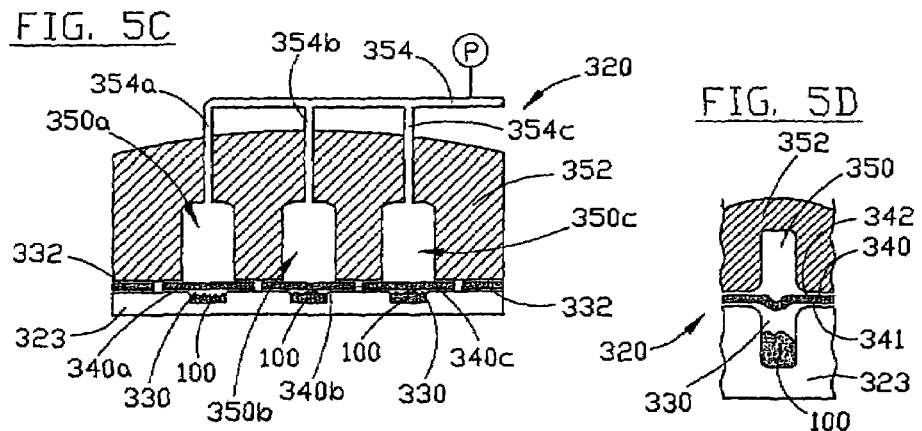
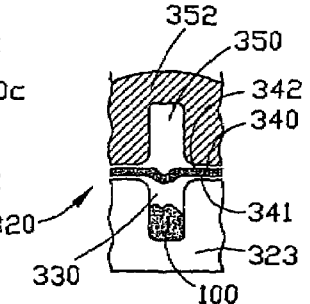

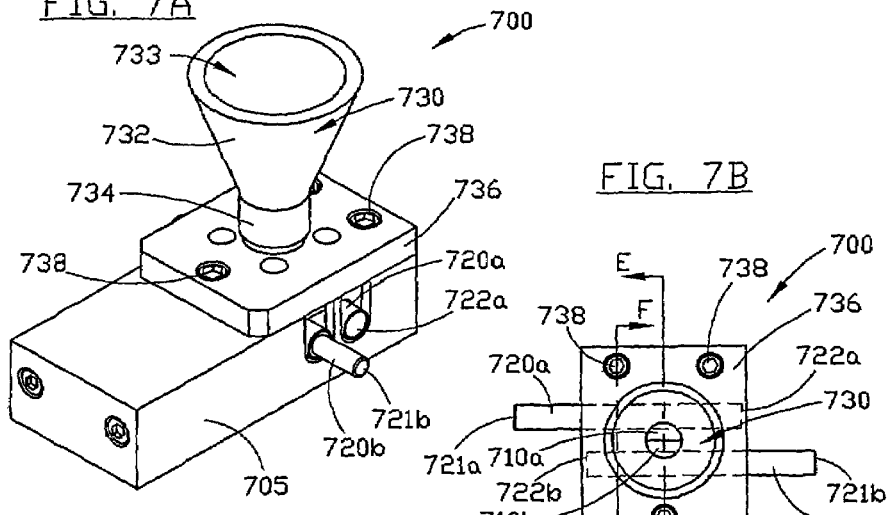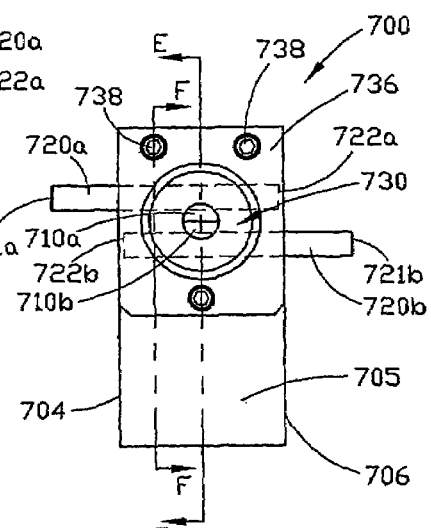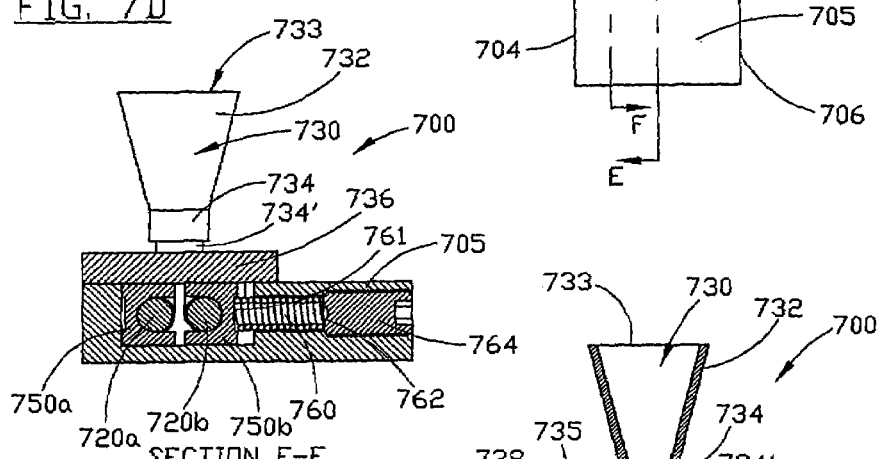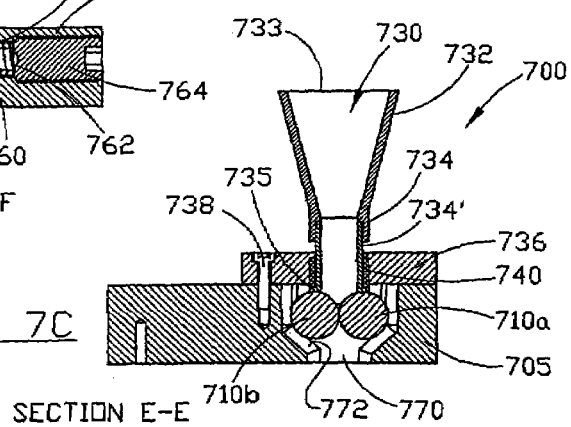

METHODS AND APPARATUS FOR MECHANICAL TREATMENT OF MATERIALS SUCH AS CATALYSTS

This application is a divisional of U.S. patent application Ser. No. 10/880,412, now issued as U.S. Pat. No. 7,111,802, to Lugmair et al., filed Jun. 28, 2004, which is a divisional application of U.S. patent application Ser. No. 09/902,552, now issued as U.S. Pat. No. 6,755,364, to Lugmair et al., filed Jul. 9, 2001, which claims the benefit of co-owned, co-pending U.S. provisional patent application Ser. No. 60/216,777entitled "High-Throughput Methods for Evaluating Heterogeneous Catalysts" filed Jul. 7, 2000 by Hagemeyer et al., which is hereby incorporated by reference in its entirety for all purposes.

BACKGROUND OF THE INVENTION

Heterogenous catalysts have a variety of known applications, in diverse fields including commodity chemicals and fine chemicals. It has long been recognized, however, that the catalytic activity and/or selectivity of heterogeneous catalysts can vary substantially due to many factors. Factors known to have a potential effect on catalytic activity and/or selectivity are described, for example, by Wijngaarden et al., "Industrial Catalysis—Optimizing Catalysts and Processes", Wiley-VCH, Germany (1998).

Combinatorial (i.e., high-throughput) approaches for evaluation of catalysts and/or process conditions are also known in the art. See, for example, U.S. Pat. No. 5,985,356 to Schultz et al., U.S. Pat. No. 6,004,617 to Schultz et al, U.S. Pat. No. 6,030,917 to Weinberg et al., U.S. Pat. No. 5,959,297 to Weinberg et al., U.S. Pat. No. 6,149,882 to Guan et al., U.S. Pat. No. 6,087,181 to Cong, U.S. Pat. No. 6,063,633 to Willson, U.S. Pat. No. 6,175,409 to Nielsen et al., and PCT patent applications WO 00/09255, WO 00/17413, WO 00/51720, WO 00/14529, each of which U.S. patents and each of which PCT patent applications, together with its corresponding U.S. application(s), is hereby incorporated by reference in its entirety for all purposes. Considered individually and cumulatively, these references teach the synthesis and screening of arrays of diverse materials, and generally, of spatially-determinative arrays of diverse materials. Typical approaches involve primary synthesis and screening (high-throughput "discovery" screening) followed by secondary synthesis and screening (more moderate-throughput "optimization" screening), and optionally, followed by tertiary synthesis and screening (e.g., typically traditional "bench scale" screening). These references also describe screening strategies in which compositionally-varying arrays are prepared (e.g., as part of a primary or secondary screen) first with broadly-varied gradients. Subsequently, "focused" libraries comprising more narrowly-varied gradients are prepared and screened (e.g., at the same level of screen) based on the results of the first screen. Such libraries or arrays of diverse materials such as catalysts can comprise binary, ternary and higher order compositional variations. See, for example, WO 00/17413 (as well as its corresponding U.S. application, Ser. No. 09/156,827 filed Sep. 18, 1998 by Giaquinta et al.) and WO 00/51720, (as well as its corresponding U.S. application, Ser. No. 09/518,794 filed Mar. 3, 2000 by Bergh et al.), each of which U.S. and PCT applications are hereby incorporated by reference in its entirety for all purposes. High-throughput process optimization, including process optimization in parallel flow reactors has also been described. See, for example, WO 00/51720, (as well as its corresponding U.S. application, Ser. No. 09/518,794 filed Mar. 3, 2000 by Bergh et al.), and additionally, U.S. patent applications Ser. No. 60/185,566 filed Mar. 7, 2000 by Bergh et al., Ser. No. 60/229,984 filed Sep. 2, 2000 by Bergh et al., Ser. No. 09/801,390 filed Mar. 7, 2001 by Bergh et al., and Ser. No. 09/801,389 filed Mar. 7, 2001 by Bergh et al., each of which U.S. and PCT applications are hereby incorporated by reference in its entirety for all purposes.

The efficiency of a catalyst discovery program is, in general, limited by rate-limiting steps of the overall process work flow. Additionally, high throughput approaches still require substantial efforts to explore vast compositional space. As such, current approaches, while offering substantial advances over previous traditional, lower-throughput approaches, can still be improved with respect to overall efficiency. Hence, there is a need in the art for improved overall research work flows for developing and evaluating heterogeneous catalysts for a particular reaction of interest. In particular, a need exists for more efficient, meaningful approaches for identifying new heterogeneous catalysts.

More specifically, a need exists for improved preparation protocols for heterogeneous catalysts. Although substantial advances have been made with respect to parallel synthesis of catalyst candidate materials, and with respect to reaction-based screening of such catalyst candidates, relatively fewer advances have focused on pretreatment of heterogeneous catalysts—after synthesis of the catalysis material or precursor thereof and before screening thereof. Typical post-synthesis catalyst treatment can include chemical treatment (e.g., precursor decomposition, oxidation, reduction, activation), physical treatment (e.g., calcining, washing), and/or mechanical treatment (e.g., grinding, pressing, crushing, sieving, and/or shaping).

Mechanical pretreatment approaches have been effected to date for combinatorial catalysis research using conventional approaches. For example, Senkan et al. reported the preparation of a combinatorial array of shaped catalysts (pellets) using conventional, serial die-pressing. See S. Senkan et al., "High-Throughput Testing of Heterogeneous Catalyst Libraries Using Array Microreactors and Mass Spectrometry", Angew. Chem. Intl. Ed., Vol. 38, No. 18, pp. 2794-2799 (1998). Grinding approaches for catalyst preparation are also known in the art, including both serial and parallel grinding protocols. (See, for example, Obenauf et al., Catalog of SPEX CertiPrep, Inc. (Metuchen, N.J.) pp. 28-39, 90-91, 104-105 and 114-119 (1999)). Schuth et al. disclose a loading device for synthesis of an array of catalysts, where the loading device is adapted for parallel transfer of the synthesized catalysts to a parallel flow reactor through a communition device. (See EP 19809477 A1). However, such conventional pretreatment protocols, such as the conventional serial pressing approaches, are not efficient enough for preparing arrays comprising larger numbers of catalysts. Moreover, conventional grinding or communiting approaches, although parallelized, suffer from other deficiencies. Such grinding approaches, as exemplified for example by the aforementioned communition protocols of Schuth et al., result in a to-be-tested catalyst candidate that includes a broad, uncontrolled distribution of catalyst particle sizes, including catalyst particle fines. Variations in the particle size distribution of candidate catalysts—as compared between reaction vessels (or channels) of a parallel reactor—can affect catalyst performance and, additionally or alternatively, can affect the flow-characteristics when screening the catalysts in a parallel flow reactor, such that in either case, direct comparison of catalysts between reaction vessels or channels is compromised. As such, there remains a need in the art to overcome such deficiencies.

SUMMARY OF THE INVENTION

It is, therefore, an object of the present invention to provide for more efficient protocols and systems for effecting mechanical treatments of materials, and especially, mechanical treatment of catalysis materials such as heterogeneous catalysts and related materials.

Briefly, therefore, in one embodiment, the invention is directed to methods and apparatus for preparing an array of materials, preferably diverse materials such as diverse catalysis materials, having a particle size distribution substantially within a predefined particle size range. Four or more materials, preferably four or more diverse materials such as diverse catalysis materials (e.g., catalysts, catalyst precursors and catalyst supports) are simultaneously crushed in four or more spatially discrete crushing zones of a parallel crusher. The four or more materials are simultaneously sieved through a first primary sieve as they are being crushed, and additionally or alternatively, intermittently between repeated crushing steps, such that in either case, for each of the four or more catalysis materials, smaller, first-sieved particles pass through the primary sieve whereas larger unsieved particles are substantially retained in the crushing zone for further crushing. If desired, the four or more materials can be simultaneously fractionated, for example, by then simultaneously sieving the first-sieved particles of each of the four or more materials through a second, secondary sieve, such that for each of the four or more materials, smaller, second-sieved particles pass through the secondary sieve whereas larger first-sieved particles are retained by the secondary sieve. As such, primary fractions of each of the four or more materials are formed, with the primary fractions having a particle size distribution substantially within a particle size range ranging from about the mesh size of the secondary sieve to about the mesh size of the primary sieve.

In a related embodiment, the invention is directed to an apparatus for parallel crushing and sieving of catalysis materials. The apparatus generally comprises a crusher body comprising four or more spatially discrete apertures or wells. Each of the four or more apertures or wells define a crushing zone having an interior crushing surface. One or more crushing elements (e.g., crushing media) are located at least partially within each of the crushing zones and are adapted for crushing materials residing in one of the four or more crushing zones. One or more primary sieves can be integral with the crusher body, and/or can define at least a portion of the interior crushing surface for each of the four or more crushing zones, and are generally adapted to simultaneously sieve each of the four or more materials as they are being crushed, or intermittently between repeated crushing steps (e.g., temporally serial cycles of crushing, sieving, crushing, sieving, etc.), such that for each of the four or more materials, smaller, primary-sieved particles pass through the primary sieve whereas larger, unsieved particles are retained in the crushing zone for further crushing.

In some aspects of this embodiment, where further fractioning is desired, the apparatus can further comprise a sieve body comprising four or more spatially discrete apertures corresponding in spatial arrangement to the four or more apertures or wells of the crusher body, with each of the four or more apertures of the sieve body having an inlet end adapted to receive primary-sieved particles passing through the primary sieve, and an opposing outlet end. One or more second secondary sieves is situated substantially at the outlet end of each of the four or more apertures of the sieve body. The one or more secondary sieves is adapted to simultaneously sieve the primary-sieved particles of each of the four or more catalysis materials, such that for each of the four or more catalysis materials, smaller secondary-sieved particles pass through the secondary sieve whereas larger primary-sieved particles are retained by the secondary sieve. The one or more primary sieves have an actual mesh size (i.e., actual opening size of the mesh) that is larger (i.e., smaller mesh-size number) than a mesh size of the one or more secondary sieves, such that primary fractions of each of the four or more catalysis materials can be formed in the apparatus. The primary fractions can have a particle size distribution substantially ranging from about the mesh size of the secondary sieve to about the mesh size of the primary sieve.

In another aspect, the invention is directed toward a method for preparing an array of catalysis materials, where four or more materials such as diverse materials, preferably diverse catalysis materials are simultaneously pressed in four or more pressing zones of a parallel press. The parallel press can preferably be a die press, an isostatic press or a roller press.

The invention is directed as well to a parallel press. The parallel press can comprise a press body comprising four or more spatially discrete apertures or wells, each of the four or more apertures or wells defining a pressing zone, and one or more pressing elements (e.g., pressing membranes, rollers, dies) adapted to simultaneously press each of four or more materials in the four or more pressing zones.

The methodologies and apparatus described and claimed herein also have application for parallel mechanical treatment of catalysis materials as well as other materials. It is contemplated and specifically considered to be part of the invention that the protocols and apparatus disclosed herein are applicable to materials generally, and to other specific categories of materials such as electronic materials (e.g., phosphors), colorants (e.g., organic or inorganic pigments), filtration materials, adsorbents, absorbents, separation media (e.g. for liquid chromatography), fluidizable particles (e.g., for fluidized bed reactors), titania (or other ceramic) nanoparticles, and pharmaceuticals (e.g, crystalline materials having pharmaceutical activity), among others.

Other features, objects and advantages of the present invention will be in part apparent to those skilled in art and in part pointed out hereinafter. All references cited in the instant specification are incorporated by reference for all purposes. Moreover, as the patent and non-patent literature relating to the subject matter disclosed and/or claimed herein is substantial, many relevant references are available to a skilled artisan that will provide further instruction with respect to such subject matter.

BRIEF DESCRIPTION OF THE DRAWINGS

FIG. 2 is a schematic diagram indicating the major mechanical treatment steps for the preparation of heterogeneous catalysts.

FIG. 3A through FIG. 3E are schematic cross-sectional views of various mechanical treatment apparatus, including a parallel press (FIG. 3A), a parallel materials handler, suitable for transfer and for various chemical and/or physical treatments (e.g., calcining) (FIG. 3B), a parallel crusher with an integral parallel sieve (FIG. 3C), an additional parallel secondary sieve (FIG. 3D) and a parallel fines collector (FIG. 3E).

FIG. 5A through FIG. 5D are schematic cross-sectional views of various embodiments of a parallel isostatic press, having a unitary common pressure chamber (FIG. 5A), or alternatively, having modular pressure chambers (FIG. 5B), or alternatively, having individual pressure chambers (FIG. 5C), each with shallow-well press bases, or having an individual pressure chamber with a deep-well press base (FIG. 5D).

FIG. 7A through FIG. 7D are a perspective view (FIG. 7A), a top sectional view (FIG. 7B), a first cross-sectional view (FIG. 7C, taken at line E-E of FIG. 7B), and a second cross-sectional view (FIG. 7D, taken at line F-F of FIG. 7B) of a roller press adapted for integration into a parallel roller press.

DETAILED DESCRIPTION OF THE INVENTION

Figure 1:
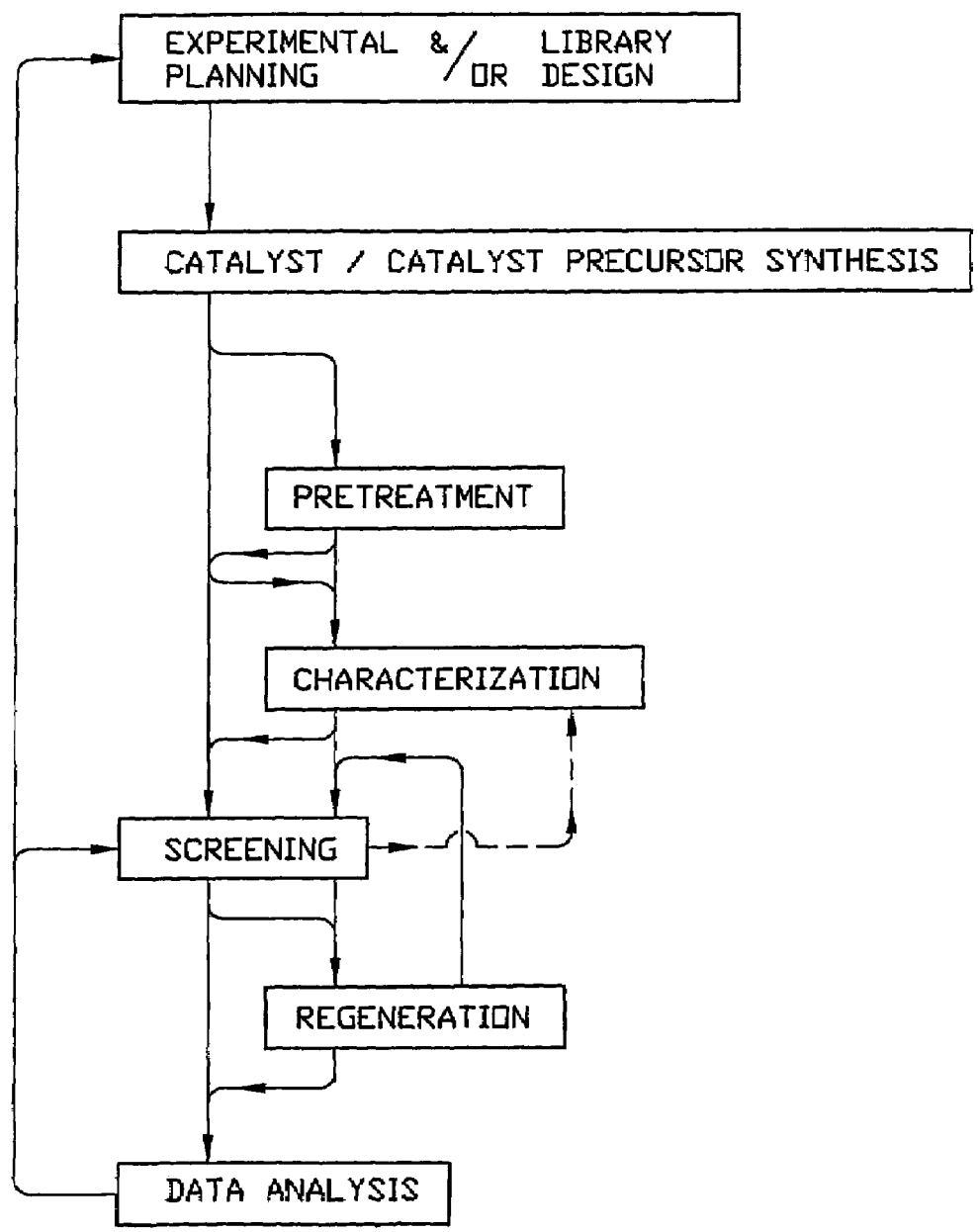
FIG. 1 is a schematic diagram indicating the major steps in a comprehensive combinatorial (i.e., high-throughput) research program for heterogeneous catalysis.

The present invention includes various mechanical treatment methodologies and apparatus for the efficient preparation of an array of materials, such as catalysis materials for heterogeneous catalysis research. In particular, this invention discloses and claims various aspects of a work flow for combinatorial (i.e., high-throughput) research, such as catalysis research, that involves parallel apparatus for simultaneously effecting mechanical treatments such as grinding, pressing, integrated crushing and sieving, and/or fractionating of such materials. In general, the catalysis materials can be catalysts (e.g., catalyst candidates), catalyst precursors and/or catalyst supports, and can be prepared in the form of shaped catalysis materials or as fractioned (e.g., crushed and sieved) catalysis materials.

Advantageously, the simultaneous protocols and parallel apparatus generally offer substantial improvements in overall throughput for preparing arrays of materials, such as catalysis materials. Additionally, in some embodiments, the protocols and apparatus for the various mechanical treatments are effected using one or more universal components (i.e., one or more shared common components), such that successive treatments can be effected without the laborious transfer of individual catalysis materials of the array. Each of these features, as well as additional features, are discussed herein.

Although described herein primarily in the context of catalysis materials, the methodologies and apparatus described and claimed herein also have application for parallel mechanical treatment of other materials. It is contemplated, for example, that such methodologies and apparatus can be used to simultaneously grind, mix, press, crush, sieve, and/or fractionate a wide range of solid materials, including without limitation, electronic materials such as phosphors, colorants such as pigments, filtration materials, adsorbents, absorbents, separation media such as liquid chromatography solid phase separation media, fluidizable particles such as for fluidized bed reactors, titania (or other ceramic) nanoparticles, and pharmaceuticals such as crystalline drugs or drug candidates (e.g., in polymorph studies), among others.

The terms used herein are generally consistent with the terms used in the provisional patent application to which this patent application claims priority. However, to clarify certain aspects, it is noted that the term "grinding" as used herein was generally referred to as "pregrinding" in the provisional patent application, the term "pressing" as used herein was variously referred to as "pressing" "compacting" and/or "pelletizing" in the provisional patent application, and the term "crushing" as used herein was generally referred to as "grinding" in the provisional patent application. Generally, all terms used herein should be interpreted as having their ordinary meaning in the art, except and to the extent that they are further defined herein.

The invention is described in further detail below with reference to the figures, in which like items are numbered the same in the several figures.

The following patent applications are related to the present application, and are specifically incorporated by reference for all purposes, including general background, methodologies, apparatus, and exemplary applications: U.S. Ser. No. 09/156,827 filed Sep. 18, 1998 by Giaquinta et al.; U.S. Ser. No. 09/518,794 filed Mar. 3, 2000 by Bergh et al.; U.S. Ser. No. 09/093,870 filed Jun. 9, 1998 by Guan et al; U.S. Ser. No. 60/185,566 filed Mar. 7, 2000 by Bergh et al.; U.S. Ser. No. 09/801,390 filed Mar. 7, 2001 by Bergh et al.; U.S. Ser. No. 09/801,389 filed Mar. 7, 2001 by Bergh et al.; U.S. Ser. No. 09/285,363 filed Apr. 2, 1999 by Petro et al.; U.S. Ser. No. 09/174,856 filed Oct. 19, 1998 by Lacy et al.; and U.S. Ser. No. 09/516,669 filed Mar. 1, 2000 by Lugmair et al, and U.S. Ser. No. 09/619,416 filed Jul. 19, 2000 by VanErden et al.

General Overview—Combinatorial Catalysis Research

With reference to FIG. 1, major steps in a comprehensive combinatorial (i.e., high-throughput) research program for heterogeneous catalysis can generally comprise one or more of the following steps:

1) Experimental Planning/Library Design
2) Synthesis of Catalyst or Catalyst Precursor Library
3) Optionally, Pretreatment of Catalyst or Catalyst Precursor Library
   a) chemical treatment (e.g. precursor decomposition, oxidation, reduction, activation),
   b) physical treatment (e.g., calcining, washing),
   c) mechanical treatment (e.g., grinding, pressing, crushing, sieving)
4) Optionally, Characterization of Catalyst or Catalyst Precursor Library (x-ray diffraction, infrared, surface area, porosity (i.e., pore size, pore volume, pore size distribution, and/or pore volume distribution), particle size, particle size distribution, metal loading, metal dispersion, etc.)
5) Screening (Reaction Based) of Catalyst Candidates in Library
   a) Flow/Semi-Continuous/Batch (Non-Flow)
   b) Liquid/Gas Phase Reactants
6) Optionally, Characterization of Screened Catalyst Candidates
7) Optionally, Catalyst Regeneration
8) Optionally, Screening (Reaction-Based) of Regenerated Catalyst
9) Optionally, Data Processing
10) Data Analysis—Performance Evaluation
11) Repeat One or More of Steps (1)-(10) (optionally, with automated resynthesis)

Preferably, all steps are optimized with respect to throughput, in order to eliminate unnecessary bottlenecks in the overall work flow. Although pretreatment steps are shown in FIG. 1 as being optional, they are nonetheless substantially significant for a comprehensive, high-throughput catalysis workflow. Generally, pretreatment steps can be categorized as chemical treatments, physical treatments and/or mechanical treatments. Although the present invention relates primarily to mechanical treatments, a person of ordinary skill in the art will appreciate that various chemical and/or physical treatments can be used in connection with the protocols and apparatus of the present invention at appropriate points of the work flow. Hence, various aspects of the present invention relate to one or more different steps of the aforementioned generalized methodology. Some aspects of the invention relate to individual steps, to a combination of steps, to a particular ordering of the steps, and/or to the methodology as a whole. Generally, the various inventive aspects can be combined in any and all possible permutations, for purposes of defining the present invention.

Generally, the methodologies and apparatus disclosed herein are useful for preparing arrays or libraries of materials, such as catalysis materials. An library of materials comprises four or more, and preferably a higher number of diverse materials as described in U.S. Ser. No. 09/518,794 filed Mar. 3, 2000 by Bergh et al. The library of materials is preferably arranged in an array, preferably comprising the diverse materials in spatially determinative regions (e.g., within different reaction vessels or modules comprising reaction vessels), and most preferably in spatially determinative and distinct regions (e.g., regions defined in one or more substrates, preferably on a common substrate in many embodiments). Modules comprising reaction vessels within a single reaction apparatus can each comprise a single substrate, and/or can collectively be considered as part of a larger substrate (e.g., where the reaction vessels and/or modules of vessels are supported by one or more common structural framework). The catalysis materials are preferably catalysts (e.g., candidate catalysts), or precursors thereof (e.g., catalyst supports), for example, as described in U.S. Ser. No. 09/518,794 filed Mar. 3, 2000 by Bergh et al.

Further details about catalysis materials, and libraries of catalysis materials, are provided below. Although described herein in connection with catalysis materials preparation for heterogeneous catalysis research, the methods and apparatus can also be used for preparing other types of materials, for other fields of research as noted above.

Parallel Pretreatment Protocols

Catalyst treatment steps, including especially mechanical treatment steps such as grinding, pressing, crushing, sieving, and/or fractionating, as well as physical and/or chemical treatment steps (e.g., calcining, oxidation, reduction, sulfurizing, washing, etc.) are preferably performed in parallel to optimize the preparation throughput for catalysis materials such as catalysts and/or catalyst precursors (including catalyst supports). Substantial technical knowledge exists in the art with respect to the mechanical treatments steps as applied to individual materials on a relative large scale, including industrial scale, pilot scale and bench-top research scale. See, for example, Fayed et al., Ed., *Handbook of Powder Science &Technology*, $2^{nd}$ Ed. (Chapman & Hall, New York, N.Y., 1997), which is hereby incorporated by reference in its entirety for all purposes.

With reference to FIG. 2, parallel mechanical treatment steps can be used to simultaneously prepare four or more (or higher numbers of) shaped catalysis materials 510 and fractioned catalysis materials 520 from starting catalysis materials 500. Generally, shaped catalysis materials 510 are catalysis materials having a definite, typically predefined shape, such as rods, cylinders, stars, cubes, tablets, hollow cylinders, spheres, ripped cylinders, rings, donuts etc., and generally (and generically) alternatively referred to herein as pellets. Fractioned catalysis materials 520 generally comprise particles of catalysis materials having a definite, and typically predetermined particle size distribution, or at least some percentage of particles falling within a particle size distribution.

The starting catalysis materials 500 are preferably catalysts (e.g., catalyst candidates), catalyst precursors and/or catalyst supports. The starting catalysis materials can be purchased from commercial vendors, and/or prepared directly, and in some embodiments, can be synthesized in situ on a synthesis substrate having common structural functionality in one or more of the subsequent mechanical treatment steps/apparatus. In particularly preferred approaches, four or more catalysis materials are simultaneously synthesized (i.e., synthesized in parallel) in four or more spatially discrete regions of a substrate (e.g., a set of parallel reaction vessels or wells). Typically, catalysis materials can be synthesized using techniques known in the art, including for example precipitation, solvent evaporation, sol-gel, spray-drying, freeze drying, impregnation, including incipient wetness impregnation (e.g., impregnation of catalyst supports such as silica, alumina, titania, zirconia, ceria, carbon, zeolites and other mesoporous or microporous materials, etc.), incipient wetness, hydrothermal synthesis and other methods known in the art or later developed.

The particular mechanical treatments to prepare shaped catalysis materials 510 or fractioned catalysis materials 520 will depend on the nature and/or form of the starting catalysis materials 500, which in turn, can depend on the synthesis technique and conditions used to prepare such starting catalysis materials 500. The starting catalysis materials 500 can, for example, be provided in the form of uniform or non-uniform pieces of various sizes, such as large chunks, moderate-sized particles, small particles, powders, flakes, granules, rods, fibers, and/or pre-formed (i.e., pre-shaped) spatial forms (e.g., pellets, including pressed pellets). Generally, for example, spray drying can result in particulates having a size ranging from about 50 μm to about 150 μm. The size and/or form resulting from other synthesis techniques, such as precipitation and/or solvent evaporation, varies substantially with the chemistries involved, and can include particle sizes ranging from fine powders, powders that have agglomerated to form moderate to larger sized particles or chunks, and/or directly-formed moderate to larger sized particles or chunks. Catalyst supports (and likewise, supported catalysts) are available in a wide spectrum of sizes and forms. Molecular sieves, generally including zeolites, and other mesoporous or microporous materials are likewise available in a variety of sizes and forms, but can for many applications, be about 0.5 to about 10 um in size after hydrothermal synthesis. In general, the particular synthesis technique, and the particular form and/or nature of the starting catalysis materials is not critical to the invention, and a person of skill in the art can select which of the various treatment strategies to employ, depending on the particular form of the starting material, and the desired form and/or nature of the catalysis materials being prepared.

According to the present invention, shaped catalysis materials 510 are prepared from starting catalysis materials 500 by simultaneously pressing four or more catalysis materials (e.g., starting catalysis materials 500 or ground catalysis materials 502) in four or more pressing zones of a parallel press, respectively, to form four or more pressed catalysis materials 504. If desired, shaped catalysis materials 510 can alternatively be formed by pressing crushed/sieved catalysis materials 514 or further fractionated catalysis materials 516 having more narrow, and typically defined particle size distributions, and/or by pressing fines 517 resulting from the sieving and/or fractionating steps. The materials being pressed can also be materials (e.g., multi-component catalysts) that were previously pressed, and then reground. In any case, the parallel press (i.e., the compactor) can generally be a device or instrument adapted to agglomerate smaller particles into larger particles for multiple materials in simultaneous (i.e., parallel) channels, by application of pressure in a compacting format. The press can be a pelletizer, a kneader, an extruder, a tableter, a roller or other pressing (i.e., compaction) device or mechanism known in the art (e.g., as known in a single channel configuration). The parallel press can be a flow-press (e.g., a flow extruder or injection molder) or a static press (e.g., a batch die press), and can generally include four or more spatially discrete pressing zones, each of the zones being defined by an interior pressing surface. The parallel press can generally also include, in each channel thereof, one or more pressing elements, such as one or more dies, rollers or pressing membranes (or portions thereof), comprising one or more surfaces against which, through which, in which, on which, or between which the catalysis materials are pressed. In some cases, the pressing elements can define at least some portion of the pressing zones. The size of the catalysis materials 500, 502 supplied to the parallel pressing zones is not critical with respect to size and/or particle size distribution, but in generally, should be sized for effective pressing thereof to form pressed (e.g., agglomerated) pellets. Typical particle sizes of supplied materials 502 are less than about 200 microns or in some cases less than about 100 microns, or in some cases even less than about 10 microns. The size of the pressed catalysis pellets 504 resulting from the pressing process is not critical, and can typically range, for example, from about 1 mm to about 1 cm in diameter and from about 1 mm to about 1 cm in length, and having aspect ratios (i.e., ratio of length to width) ranging from about 10 to about 1/10, from about 1 to about 1/5, and from about 1 to about 1/2 and most preferably being about 1. Typical pressing pressure can vary depending on the type of press, the type of catalysis materials, and other pressing conditions, such as temperature, additives, etc., and can be about 500 psi or higher, and can typically range from about 1000 psi to about 75,000 psi, alternatively from about 10,000 psi to about 60,000 psi, from about 20,000 psi to about 50,000 psi, or from about 25,000 psi to about 40,000 psi. Additional details, and preferred embodiments for parallel presses (e.g., including parallel die presses and parallel isostatic presses) and simultaneous pressing protocols are discussed below in connection with FIGS. 3A, 3B, 4C, 5A through 5B, and 7A through 7D.

Optionally in some embodiments, such as where the four or more starting catalysis materials 500 are large chunks or otherwise too large (or for other reasons, such as particle size inhomogeneity, or compositional inhomogeneity, or for mechanical reasons, or to allow for chemical pretretment or characterization) to provide for satisfactory direct pressing, the four or more catalysis materials can be simultaneously ground, before pressing, in four or more spatially discrete grinding zones of a parallel grinder, respectively, to form four or more ground catalysis materials 502. Generally, grinding can be effective for breaking apart (i.e., deagglomerating) larger particles to form smaller particles, as well as to change the morphology of the particles (e.g., breaking down crystallites to expose the interior thereof). The parallel grinder can include four or more spatially discrete grinding zones defined by an interior grinding surface. The parallel grinder can also include, in each channel, one or more grinding elements. In some embodiments, the one or more grinding elements can define at least a portion of the grinding surface. The grinding elements can be grinding media of any type, including for example grinding balls, grinding rods, grinding pins or other milling elements known in the art. Suitable choice of materials for the interior grinding surfaces and the grinding elements can be made by persons of skill in the art. Typically, for example, the interior grinding surfaces of each of the four or more grinding zones can be the same as those described below, generally, for the parallel grinder, pressor, crusher and siever. Typically, grinding is effected without substantial regard to particle size and/or particle size distribution, with grinding being at least effective for subsequent pressing of the ground catalysis materials 502, optionally with other treatments as described below. Grinding to a fine powder is adequate for many catalysis materials for subseqeuent pressing. Further, grinding is typically effected without removal of fines and/or other fractioning of the various resulting particle sizes of ground particles, but such fractioning could be employed in some embodiments (e.g., via sieving while the catalysis materials 500 are being ground). The resulting ground catalysis materials 502 (e.g., catalysts or catalyst precursors) will typically comprise particles with varied particle-size distribution (e.g., distribution factor of about 2-3), from fines to about 1 mm or less. The target size for the ground catalysis materials 502, can depend on the type of press, as well as on the size (e.g., diameter) of the reaction zone (e.g., fixed-bed reaction zone), as well as on the particular grinder type, and grinding conditions.

One or more supplemental materials 506—such as diluents (e.g., silica, silicon carbide, titania, alumina, etc.), binders (e.g., benzoic acid, methyl cellulose, graphite, colloidal inorganics, silica, alumina, titanium dioxide, etc.), additional co-catalysts or catalyst precursors, dispersing agents, or grinding aids, among others—can be mixed with the ground catalysis materials 502 after grinding and prior to pressing. Alternatively, such supplemental materials 506 can be mixed in situ in the four or more grinding zones during grinding (not represented in FIG. 2). The one or more supplemental materials 506 can also so be mixed with the starting catalysis materials 500 (e.g., without grinding, or prior to grinding). When mixing is desired, the four or more catalysis materials are preferably simultaneously mixed with one or more components (such as one or more diluents) in four or more spatially discrete mixing zones of a parallel mixer, respectively. The one or more supplemental materials 506 can be a solid or a liquid, as added to the catalysis materials. For example, a slurry of materials can be formed to facilitate mixing and to assist in or otherwise affect grinding.

The four or more pressed catalysis materials 504 can themselves be the shaped catalysis materials 510, or alternatively, can be further treated (e.g., physically and/or chemically) to form the shaped catalysis materials 510. Additionally, the four or more pressed catalysis materials 504 can be reground, and repressed, with or without and before or after such further treatment. Such repeated grinding, pressing, regrinding and repressing operations can improve mixing and, therefore, the homogeneity of the catalysis materials. In some embodiments, the press pressure can be increased in the second (or other additional pressing steps) to compact the catalysis materials to a more dense form.

According to the invention, fractioned catalysis materials 520 are prepared by simultaneously crushing four or more catalysis materials (e.g., starting catalysis materials 500, pressed catalysis materials 504 (with or without grinding prior to pressing, and with or without mixing prior to or during or after grinding), or even shaped catalysis materials 510) in four or more spatially discrete crushing zones of a parallel crusher, respectively, to form four or more crushed catalysis materials 512. During the crushing process, or alternatively, intermittently between each of a series of two or more repeated crushing steps, a portion of the crushed particles are removed simultaneously from each of the four or more crushing zones. The portion of crushed particles are preferably removed as the catalysis materials are being crushed. In a preferred approach, the removal is effected by simultaneously sieving each of the four or more catalysis materials 500, 504 and or crushed catalysis materials 512 through a first primary sieve as they are being crushed to form four or more first-sieved particles 514. As such, for each of the four or more catalysis materials, smaller, first-sieved particles 514 pass through the primary sieve whereas larger unsieved particles are retained in the corresponding crushing zone for further crushing. The removed portion (e.g., the first-sieved particles 514) of each of the four or more catalysis materials are then simultaneously fractioned (e.g., by simultaneously separating fines therefrom). More generally, simultaneous fractionating can be effected by simultaneously sieving through a second, secondary sieve, such that for each of the four or more catalysis materials, smaller, second-sieved particles (e.g., fractionated catalysis materials 516) pass through the secondary sieve whereas larger first-sieved particles 514 are retained by the secondary sieve. In this manner, each of the sieved catalyst or catalyst precursor or catalyst support comprises one or more sized-fractions, each of the sized fractions comprising particle sizes having a substantially narrow particle-size distribution, or alternatively, at least excluding certain larger or certain smaller particle sizes. Specifically, primary fractions of each of the four or more catalysis materials are formed, having a particle size distribution substantially within a particle size range ranging from about the mesh size of the secondary sieve to about the mesh size of the primary sieve. Preferably, at least about 90%, more preferably at least about 95% and most preferably at least about 98% of the primary fraction particles are within the particle size range bounded by the mesh sizes of the primary and secondary sieves. Advantageously, improved sieving efficiencies can be achieved by the methods of the invention, including especially primary sieving of relatively smaller particles as larger particles are being crushed (or intermittently between repeated crushing steps). Hence, according to the invention, the primary fraction of each of the four or more catalysis materials comprises at least about 20% by weight of the total catalysis material being crushed and sieved, preferably at least about 40%, more preferably at least about 50%, still more preferably at least about 60% and most preferably at least about 70%, by weight (depending of course, on the target particle size range distribution and other factors).

If desired, further fractionating steps (beyond at least the removal of fines) can be effected for each of the four or more catalysis materials. Specifically, for example, the second-sieved particles of each of the four or more catalysis materials can be simultaneously sieved through a third, tertiary sieve, such that for each of the four or more catalysis materials, smaller, third-sieved particles pass through the tertiary sieve whereas larger second-sieved particles are retained by the tertiary sieve. In this manner, secondary fractions of each of the four or more catalysis materials are formed. The secondary fractions can have a particle size distribution substantially within a particle size range ranging from about the mesh size of the tertiary sieve to about the mesh size of the secondary sieve. Preferably, at least about 90%, preferably at least about 95%, and most preferably at least about 98% of the secondary fraction particles are within the particle size range bounded by the mesh sizes of the secondary and tertiary sieves. Likewise, the third-sieved particles of each of the four or more catalysis materials can be simultaneously sieved through a fourth, quaternary sieve, such that for each of the four or more catalysis materials, smaller, fourth-sieved particles pass through the quaternary sieve whereas larger third-sieved particles are retained by the quaternary sieve, such that tertiary fractions of each of the four or more catalysis materials are formed, with the tertiary fractions having a particle size distribution substantially within a particle size range ranging from about the mesh size of the quaternary sieve to about the mesh size of the tertiary sieve. Preferably, at least about 90%, preferably at least about 95%, and most preferably at least about 98% of the tertiary fraction particles are within the particle size range bounded by the mesh sizes of the tertiary and quaternary sieves.

Some of the fractions, or at least the fines 517 of the catalysis materials, can be recycled back to the parallel press for incorporation into additional preparation steps.

In the parallel crusher, each of the four or more crushing zones are defined by an interior crushing surface. In a preferred embodiment, the primary sieve is integral with the parallel crusher, and can define at least a portion of the interior surface of each of the four or more crushing zones, to allow for the removal of a portion of the crushed particles from the crushing zone as the catalysis materials are being crushed. In other embodiments, however, removal of portion of the crushed particles can be effected by other than sieving means, including for example, by differential fluidic suspension and/or by other separating approaches. Crushing can be effected by numerous methods known in the art, including for example by impact of the catalysis materials against an interior surface of the crushing zone (e.g., due to agitation or shaking of the parallel crusher), by impact against one or more crushing elements such as crushing media (e.g., crushing balls or crushing rods within each of the crushing zones, and/or by pushing through a mechanically stable die (e.g., communition), etc., and in either case, optionally with parallel vibration to facilitate sieving during or intermittent with crushing steps. In one embodiment, a die can be used both for parallel crushing as well as for sieving as the primary sieve. Such various methods can be employed individually or together to get the desired crushing action.

The primary sieve associated with each of the four or more crushing zones can be four or more separate, individual primary sieves such that the four or more crushed catalysis materials are sieved through the separate, individual sieves. Alternatively, the primary sieve can be a unitary sieve having at least two or more discrete sieving regions, or in some embodiments, four or more discrete sieving regions, through which at least two of the four or more catalysis materials, and preferably four or more of the catalysis materials are sieved. The secondary sieve, as well as the ternary seive, quaternary sieve, or higher-ordered sieves can be independent apparatus, or preferably, can also be integral with or integrally combined with the parallel crusher apparatus to form an integral crushing/sieving/fractionating device. Likewise, the secondary (or higher-ordered) sieve(s) can be a unitary sieve having at least two or more discrete sieving regions, or in some embodiments, four or more discrete sieving regions, through which at least two of the four or more catalysis materials, and preferably four or more of the catalysis materials are sieved.

The absolute size of the crushed and sieved particles is generally not narrowly critical, and can depend upon factors such as the end-use application involved and desired characteristics. For evaluation of catalysis materials in a heterogeneous catalysis research program, the average particle size of one or more fractions can generally range from about 10 microns to a size that is about ⅕th of the diameter of the reaction zone in which the catalysis material will be evaluated, and preferably from about 50 microns to about ⅒th of the reaction zone diameter, and most preferably from about 1/20th to about ⅒th of the reaction zone diameter. Hence, for many reaction systems, an average particle size can range from about 50 microns to about 5 mm, preferably from about 70 microns to about 2 mm can be adequate. The mesh sizes for the primary and/or secondary sieves can vary consistent with such dimensions. For heterogeneous catalysis research involving relatively small volume reaction systems (having for example, inside diameters of about 4 mm for the reaction zone), an average particle size of about 50 microns to about 1 mm is typical, and 70 microns to about 0.4 mm is preferred. For reaction evaluation systems having larger reaction zones, the average particle sizes can generally range from about 50 microns to about 2.5 mm, preferably from about 70 microns to about 1.25 mm. In general, the primary sieve and secondary sieve for each material can have mesh size appropriate for the desired range of particle sizes. Likewise, tertiary, quaternary and higher-ordered sieves can have mesh sizes appropriate for the desired average particle size of the secondary, tertiary and other fractions. The particular particle size distribution for such applications is also not critical to the invention, and can generally vary according to preferences known in the art. In some applications, it may be desirable to have relatively narrow particle size distributions, whereas in other applications, the particle size distribution can be broader. Significantly, such average particles sizes (as recited above) can be achieved in various particle size distributions according to the methods and apparatus of the present invention.

In additional embodiments for preparing fractioned catalysis materials, prior to parallel crushing/sieving/fractionating, a plurality of catalysts, catalyst precursors, or catalyst supports, and preferably four or more, or higher numbers thereof, as described, are simultaneously ground to form a plurality and preferably four or more ground catalysis materials 502, and additionally, or alternatively, simultaneously pressed (i.e., compacted) in a parallel press (i.e., a parallel-channel compactor) to form a corresponding four or more pressed catalysis pellets 504. The parallel grinding and/or pressing can be generally as described above in connection with preparation of shapedcatalysis materials 510. In fact, as noted, shaped catalysis materials 510 can themselves be fed through the parallel crushing/sieving/fractionating device. Likewise, the mechanical treatment can include parallel mixing (before, during or after grinding of the catalysis starting materials 502), generally as described above in connection with preparation of shaped catalysis materials 510. Further, as described, the grinding and pressing steps can be repeated (with or without additional chemical and/or physical treatments and/or characterization) prior to crushing and sieving, to improve homogeneity and/or to change the morphology of the particles.

If desired, the fractionated catalysis materials 516 can also be further treated at this stage (e.g., washed), preferably in parallel, to form four or more further treated catalysis materials 518. The particular one or more fractions of the four or more crushed/sieved/fractioned catalysis materials (e.g., catalysts, catalyst precursors and/or catalysts supports) can then be selected for further catalyst preparation steps, and preferably, in simultaneous preparation steps, or can be used directly in the end application of interest.

As noted, physical treatment, chemical treatments and characterization steps can also be used, in conjunction with the various mechanical treatment steps of the invention. For example, the four or more catalysis materials (e.g., starting catalysis materials 500, ground catalysis materials 502, pressed catalysis materials 504, crushed catalysis materials 512, sieved catalysis materials 514, and/or fractioned catalysis materials 516) can be simultaneously calcined, and/or simultaneously chemically treated (e.g., oxidized, reduced, sulfurized, etc.) and/or simultaneously characterized for a property of interest. In FIG. 2, the timing of some such additional treatment activities are shown, for example for calcining (indicated as a circled "A" in FIG. 2), chemical treatments (indicated as a circled "B" in FIG. 2). Also, each of the four or more catalysis materials (in one or more intermediate stages, as pressed catalysis materials 510 and/or as fractioned catalysis materials 520) can be characterized, and preferably simultaneously characterized for a property of interest. For heterogeneous catalysis materials and other materials, for example, characterization can be effected in parallel for porosity (including for example, pore size, pore size distribution, pore volume and/or pore volume distribution), crystallinity, identity, composition, morphology, surface area, particle size, particle size distribution, metal loading, metal dispersion, oxidation state, coordination number, phase formation, acidity, basicity, and dielectric among other properties. In FIG. 2, the timing of representative characterization are shown (indicated as a circled "C" in FIG. 2). With reference to FIG. 2, for example, the starting materials 500 (including optionally supplemental materials 506) can be physically treated (e.g., calcined) or chemically treated (oxidation, reduction, etc.) and/or characterized before the grinding step, and/or the ground materials 502 can be physically treated, chemically treated or characterized between the grinding and pressing steps, and/or the pressed materials 504 can be physically treated, chemically treated or characterized after the pressing step. In some cases, it may be preferable to grind the materials 500, and then calcine and/or chemically treat the ground materials 502, and then to regrind the treated materials. Such repeated cycles of grinding, treating, grinding, treating, grinding, treating, etc. steps can improve compositional homogeneity of the materials. Other particular strategies for incorporating chemical, physical treatments, and/or characterization steps into the overall workflow are known in the art, and readily applied to and integrated with the parallel mechanical treatment steps of the invention, and as so integrated, are considered part of this invention. In general, such further treatments and/or characterizations steps are preferably effected simultaneously for each of the four or more shaped catalysis materials and/or four or more fractioned catalysis materials. In some embodiments, such treatments and/or characterization steps are preferably effected in situ with the chemical and/or physical treatment zones and/or the characterization regions including at least a portion of the structure in which the catalysis materials were or will be mechanically treated.

The interior surfaces of the grinding zones, pressing zones, mixing zones and/or sieving zones, as well as any grinding elements, pressing elements, crushing elements, or sieves (or generally, other materials having contact with the four or more materials being treated), can be of any suitable material, and preferably a material that is inert to the chemical reaction being investigated. Such materials can generally include metals, ceramics and plastics, and preferably include hardened steels, glass, ceramics, including for example, silica, zirconia, ceria, steel, stainless steel, aluminized steel, silicon carbide, silicon nitride, nitrided titanium, tungsten carbide, acrylics, polypropylene, polycarbonate, polystyrene, polytetrafluoroethylene (PTFE) and other materials known in the art.

Providing an array comprising fractioned, different catalysis materials 520 as described herein for use in a parallel reaction vessel for reaction screening is advantageous over the prior art methods. This is particularly true when bulk as-synthesized catalysis materials are first simultaneously ground, simultaneously pressed, and then simultaneously crushed/sieved/fractionated to form the fractioned catalysis materials 520. Without being bound by theory not specifically recited in the claims, the grinding step increases the surface area of the catalyst, improves the compositional homogeneity, and/or changes exposed active sites (e.g., by breaking open and exposing interior of crystallites) for example, to improve the solid-gas reactions during calcination and also to improve solid-gas reactions and other interactions (e.g., adsorption, desorption) during the catalytic reaction. The pressing (i.e., pellitization) of the powder increases the contact between grains, particularly with repeated cycles of grinding and pressing, allowing more efficient solid state reactions and phase transformations during calcination. Further, employing candidate catalysts or other fractioned catalysis materials comprising appropriate size distribution minimizes other potential problems. Such problems can include, in a parallel fixed bed screening reactor, for example (depending on the size of the undesirable non-fractioned particles and the height of a reaction bed or zone): channeling of gas through the catalyst in one or more channels of the fixed bed reactor, bypassing of catalyst materials along the side of the reaction zone, fluidization of fine particles in one or more channels of the fixed bed reactor, excessive pressure drop across the catalyst bed in an individual one or more channels, and unequal flow between channels of a parallel flow reactor. For example, in preferred embodiments, fluid mechanics in a tubular reactor are enhanced by providing a catalyst particle diameter ranging from about 0.2 to about 0.005, and preferably from about 0.1 to 0.01 times the reaction zone diameter. For example, a 4 mm ID tubular reactor should be charged with 400 um to 40 um diameter catalyst particles. The potential importance of the pretreatment steps of pressing, crushing and sieving are demonstrated, for example, in Example 1. Hence, parallization of pressing, crushing and sieving is important for a high-throughput research program for heterogeneous catalysis.

Integral Parallel Pressing/Crushing/Sieving/Fractionating Device

With reference to FIGS. 3A through 3E, an exemplary parallel pressing/crushing/sieving device 10 (i.e., compaction, milling and sieving apparatus) comprises a parallel pellet press 20 having an array (with two or more, preferably four or more, preferably a higher number, n) of spatially discrete pressing zones 30 (e.g., compartments or cavities) defined by press walls 22 of a press body 23, press bottom 24, lower dies 26, and spring-loaded upper dies 28, as depicted in FIG. 3A. The pressing zones 30 can be at least partially defined by spatially discrete apertures (as shown) or wells, or dimples. The press bottom 24 of the array of chambers is preferably sealed. An array of bulk catalyst candidates or precursors 100 are placed into the cavities 30. The parallel press also includes one or more pressing elements adapted to simultaneously press each of the four or more catalysis materials in the four or more pressing zones. As shown in FIG. 3A, a press lid 32 of the press has a plurality (preferably, n) of spring-loaded upper dies 28 attached thereto, and situated over the array of catalysts/precursors 100. A vertical force, F, is applied to the press lid 32, to effect parrallel compaction of the plurality of catalysts/precursors 100. The spring loaded dies 28 allow the same force to be applied to the catalysts 100 in each cavities 30, even if the cavities are not filled to the same extent.

The four or more die sets, each comprising an upper and/or lower dies 28, 26, can be removed, as shown in FIG. 3B, to allow the pressed catalyst pellets 102 to be punched out of the press body 23. The catalysts can then be ground or calcined, for example, using conventional approaches. Alternatively, the catalysts 100 or catalyst pellets 102 can by calcined in situ in the press body 23 (FIG. 3B). In such an approach, a reactive or inert gas can be present in the pressing zones (in a static approach) and/or can be forced through the pellets (in a flow-based approach), during the calcination.

Alternative parallel press configurations or designs can also be employed in place of the design shown in FIGS. 3A and 3B. One preferred alternative, a parallel isostatic press, suitable for use independently of, or in connection with the integral pressing/crushing/sieving device 10 is depicted in FIGS. 5A through 5D, and discussed in connection therewith. Another alternative press is a parallel roller press, suitable for use independently of, or in connection with the integral pressing/crushing/sieving device 10 is depicted in FIGS. 7A through 7C and discussed in connection therewith.

An exemplary, integral parallel crushing/sieving device 50, depicted schematically in FIG. 3C, can comprise a crusher body 53 made of a suitable abrasion-resistant material (e.g., alumina). The crusher body 53 can comprise a plurality of crushing zones 70 (e.g., compartments), defined generally by interior crushing surfaces. The crushing surfaces can be defined at least partially for example, by apertures having interior side walls 52 or wells (not shown in FIG. 3C) The bottom plate 54 of the parallel crusher 50 can comprise a plurality of apertures 55 generally spatially arranged to correspond to the plurality of apertures defining the crushing zones 70, and can secure a primary sieve 58 against the crusher body 53 such that the primary sieve 58 is integral with the parallel crusher 50, and such that spatially discrete regions of the sieve 58 define the bottom interior surface of the crushing zones 70. Suitable crushing elements or instruments, such as a set of four or more crushing pins 60, can protrude downward from an upper plate 62 of the crusher 50, and extend into the crushing zones 70 for crushing against interior crushing surface defined by side walls 52. The upper plate 62 and crushing pins 60 can be moved, for example, in a substantially orbital/orbiting motion, and/or in a substantially vertical motion and/or in a substantially rotating motion within each of the four or more crushing zones 70 of the parallel crusher 50, to crush the four or more catalyst pellets 102 against the walls 52 of the crusher body 53 to form crushed catalyst or precursor particles 104, 106, 108. Other suitable crusher arrangements can also be effected. The crushing elements, such as crushing pins 60 and upper plate 62, can also define at least a portion of the crushing surface defining the crushing zone 70. The crushing zone 70 (i.e., crushing compartment) walls 52 and the crushing pins 60 are preferably hard and abrasion resistant. A primary sieve, 58, such as a coarse sieve, allows relatively smaller catalyst particles 106, 108 to fall through the apertures 55 once the particles have been ground sufficiently to be of a size equal to or smaller than the maximum allowable particle size passable through the primary sieve 58, while allowing relatively larger particles 104, to be retained above the primary sieve 58.

Figure 4A:
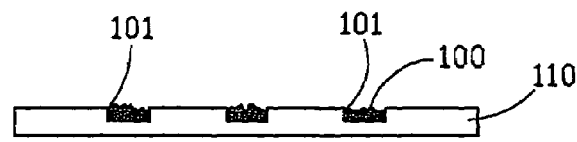
FIG. 4A through FIG. 4E are schematic cross-sectional views of various mechanical treatment apparatus having at least some common (i.e., shared) components or subcomponents, including a parallel synthesis substrate (FIG. 4A), a parallel (pre)grinder (FIG. 4B), a parallel press (FIGS. 4C), a parallel crusher with an integral parallel sieve (FIG. 4D), and an alternative configuration of a parallel crusher with a plurality of integral, curvilinear sieves (FIG. 4E).
Figure 4B:
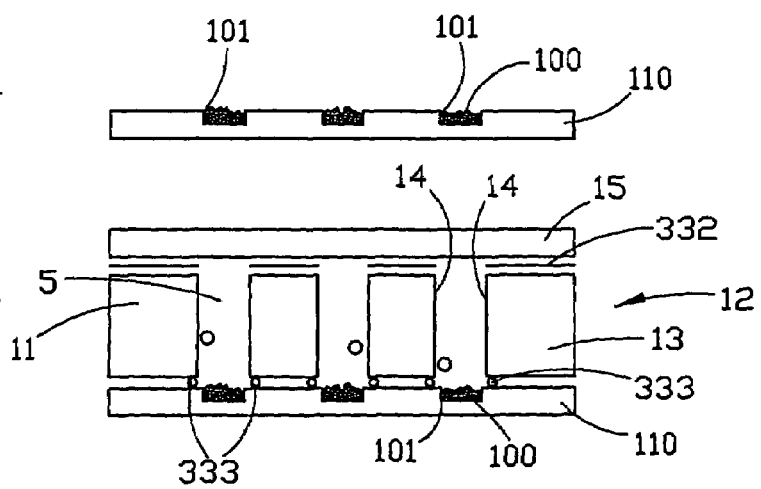

Alternative parallel integral crushing/sieving devices can also be employed in place of the design shown in FIG. 3C. One alternative, a parallel crusher using one or more crushing elements (e.g., crushing media such as crushing balls) within each of the plurality of crushing zones 70 (rather than crushing pins 60), is shown in FIG. 4D and discussed in connection therewith. In a variation of this alternative embodiment, the crusher body can comprise four or more wells, with the one or more primary sieves situated substantially at the open end of the four or more wells. As such, the four or more wells and the one or more primary sieves together define the crushing zones within each well. The four or more crushing elements in this embodiment can be a set of four or more crushing media (e.g. crushing balls) adapted for impacting motion within the four or more crushing zones of the crusher body, respectively. Another alternative, a parallel finger-die crusher, is shown in FIGS. 6A through 6D, and discussed in connection therewith. The geometry of the sieve with respect to each of the aforementioned embodiments is not narrowly critical, and can include substantially planar sieves or sieves that define a curvilinear surface such as a portion of a sphere or a portion of a cylinder, as shown, for example, as sieves 58 in FIG. 4E. Other approaches can also be used to effect crushing within the crushing zone, including for example, gear-type crushing elements such as substantially planar gears or conical-shaped ridged gears, interfacing with similarly geared surfaces, roughened surfaces and/or smooth surfaces. The interfacing surface can have an offset shape, such as an offset conical shape, relative to the shape of the gear or geared surface, such that an opening or gap is defined at the top wider end and is sized to receive uncrushed material. The distance between the gear or geared surface and the corresponding interfacing surface can then narrow to crush particles to the desired size. Each of such alternative integrated crushing/sieving devices are suitable for use independently of, or in connection with the integral pressing/crushing/sieving/fractioning device 10 of FIGS. 3A through 3E, as well as in connection with the universal component embodiment depicted and described in connection with FIGS. 4A through 4D.

The plurality of catalysis materials (e.g., catalysts/precursors), each now having a size distribution that includes a variety of particle sizes (e.g., particles 104, 106, 108), can be fractionated (e.g., further sieved) in parallel as follows. Relatively large particles 104 are retained, as noted, by sieve 58 in the parallel grinder/sieve 50. A parallel fractionating device can comprise a sieve body 83 comprising four or more spatially discrete apertures or wells corresponding in spatial arrangement to the four or more apertures or wells of the crusher body. Each of the four or more apertures of the sieve body have an inlet end adapted to receive primary-sieved particles passing through the primary sieve, and an opposing outlet end. The device also comprises one or more second secondary sieves 88 situated substantially at the outlet end of each of the four or more apertures of the sieve body 53, the one or more secondary sieves 88 being adapted to simultaneously sieve the primary-sieved particles of each of the four or more catalysis materials, such that for each of the four or more catalysis materials, smaller secondary-sieved particles pass through the secondary sieve whereas larger primary-sieved particles are retained by the secondary sieve.

More specifically, with reference to FIGS. 3D and 3E, smaller particles, 106, 108, can be allowed to fall into a plurality of cavities 90 defined by walls 82 of a fine sieve body 83 of a parallel fine sieve apparatus, 80. The parallel fine sieve apparatus 80 further comprises a secondary sieve 88, such as a fine sieve, held in place by a bottom 84 of the sieve 80. The bottom 84 comprises a plurality of apertures 85. The secondary sieve 88 is sized to allow relatively smaller-sized particles 108 (e.g., fines), to fall through the apertures 85, while allowing relative larger particles 106 to be retained above the secondary sieve 88. Additional parallel sieves (not shown) can likewise be employed, depending on the number of desired fractions. Some of the catalysis material particles 108 (e.g., catalyst or precursor particles) are small enough such that they fall through the secondary fine sieve 88, and can thereby be allowed to fall into a plurality of cavities 130 defined by walls 122 of a fines collector body 123 of a parallel fines collector 120. The parallel fines collector 120 further comprises a bottom 124. The smaller particles 108 (e.g., fines) may be repressed, recrushed or reground, and resieved. The sieving units may generally also include vibrational agitation to help fractionate the catalyst particles/powder. Other motive forces, such as pneumatic fluid forces, are likewise contemplated to help move catalyst particles through the various sieves.

The parallel press 20, parallel crusher 50 (having integral parallel primary sieve 58), and one or more parallel fractionating devices 80, 120 are modular components of the integral parallel pressing/crushing/sieving/fractionating device 10 of the invention. Each of such modular components can be substituted with other components having the same or equivalent functionality with respect to parallel pressing, parallel crushing, parallel sieving while crushing, and parallel fractionating of catalysis materials.

Universal Components of Parallel Mechanical Treatment Devices

According to another aspect of the invention, an array of catalysis materials is prepared using two or more parallel mechanical treatment apparatus, where at least some commonality of components exists between the two or more apparatus. Additionally, commonality of components can also exist between one or more mechanical treatment apparatus and one or more physical or chemical treatment apparatus. Advantageously, the universality of such components can allow for workflows having a reduced number of material transfers. Such time and labor savings are substantial, particularly in connection with large numbers of materials, small volumes of materials, and difficulties associated with handling of so many, small-volume materials.

In a preferred approach, at least some commonality of components exists between components of parallel pressing/crushing/sieving/fractionating devices. These devices, considered individually or as integral sub-devices of an integrated apparatus, generally comprise (i) a parallel press suitable for pressing four or more catalysis materials in four or more spatially discrete pressing zones, respectively, to form four or more pressed catalysis materials, (ii) a parallel crusher for simultaneously crushing the four or more pressed catalysis materials in four or more spatially discrete crushing zones, respectively, to form four or more crushed catalysis materials, (iii) a parallel primary sieve for simultaneously sieving each of the four or more catalysis materials through a first primary sieve as they are being crushed, such that for each of the four or more catalysis materials, smaller, first-sieved particles pass through the primary sieve whereas larger unsieved particles are retained in the crushing zone for further crushing, and (iv) a one or more parallel supplementary sieves (e.g., a parallel secondary sieve) for simultaneously sieving the first-sieved particles of each of the four or more catalysis materials through one or more supplementary sieves, whereby one or more fractions having a predetermined size range is formed for each of the four or more catalysis materials.

Figure 4C:
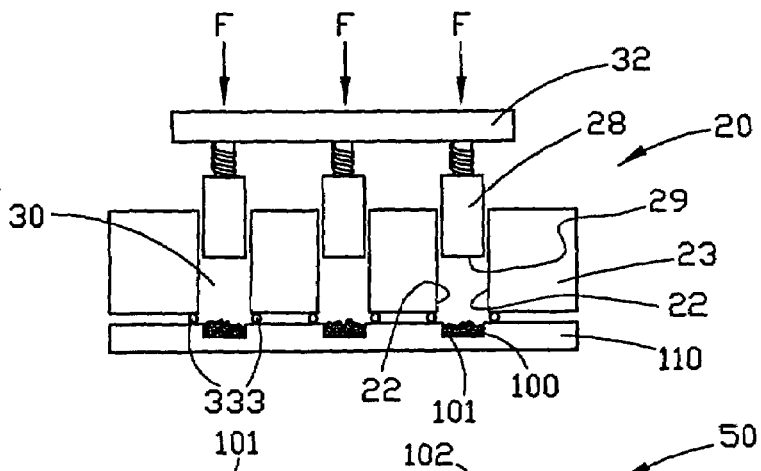
Figure 4D:
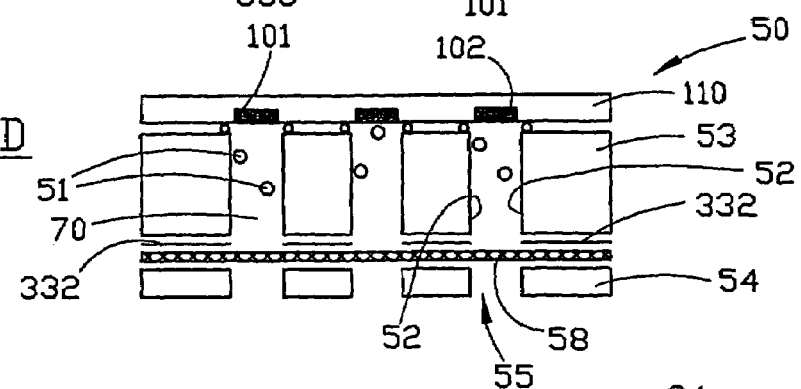
Figure 4E:
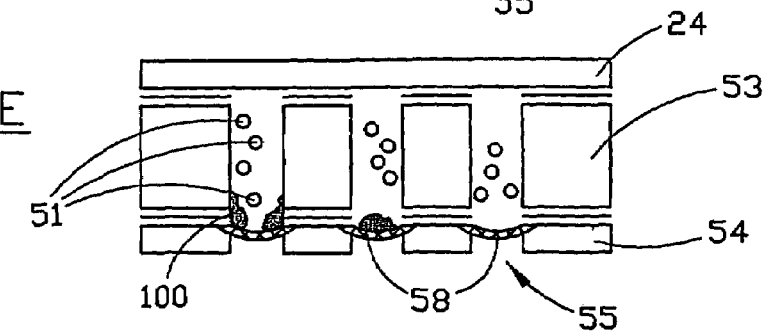

With reference to FIGS. 4C and 4D, as noted above, each of the four or more pressing zones 30 (FIG. 4C) are defined by an interior pressing surface, and each of the four or more crushing zones 70 (FIG. 4D) are defined by an interior crushing surface. The pressing surface of each of the pressing zones 30 is defined by press walls 22 of press body 23, by a bottom surface 29 of upper die 28 and by a well 101 defining a synthesis surface in a synthesis substrate 110. The crushing surface of each of the crushing zones 70 is defined by side walls 52 of crusher body 53, by a spatially discrete region of a unitary primary sieve 58, and by a well 101 defining a synthesis surface in a synthesis substrate 110. One or more seals, such as o-rings 333 (FIG. 4C) or a unitary gasket 332 (FIG. 4D) can be used to seal the press body 23 and the synthesis substrate 110 (FIG. 4C) and to seal the crusher body 53 and the synthesis substrate 110 (FIG. 4D), respectively. One or more crushing balls 51 are used in each of the crushing zones 70. Significantly, at least some portion of the interior pressing surface is the same as at least some portion of the interior crushing surface. That is, at least one component is common to, and universal for, both the parallel press and the parallel crusher. With further reference to FIGS. 4C and 4D, for example, the press body 23 of the parallel press 20 can be the same structural component as the crusher body 53 of the parallel crusher 50. Furthermore, the synthesis substrate 110 is common to each of the parallel press 20 and the parallel crusher 50, and allows for en-banc material transfer between these devices (without the tedious, individual serial transfer of the pressed materials). The transition from the parallel press of FIG. 4C to the parallel crusher/sieve of FIG. 4D can be effected, for example, by replacing the plurality of press elements (e.g., upper dies) 28 with the primary sieve 58, adding a set of crushing balls, and then inverting the parallel press of FIG. 4C. Similar commonality of components is contemplated with respect to the press body 23 of the parallel press 20 and the crusher body 53 of the parallel crusher 50, as shown in FIGS. 3A and 3C, respectively.

As another exemplary embodiment, the parallel press 20 and/or the parallel crusher 50 with integral primary sieve 58 can have commonality of component structure with upstream apparatus of the overall workflow. Specifically, for example, with reference to FIG. 4B, each of the four or more grinding zones 5 of a parallel grinder 12 are defined by interior grinding surfaces, such grinding surfaces being defined by side walls 14 of a grinder body 13, by spatially discrete regions of grinder cover plate 15, and by a well 101 defining the synthesis surface in a synthesis substrate 110. One or more seals, such as o-rings 333 or a unitary gasket 332 can be used to seal the grinder body 13 and the synthesis substrate 110, and to seal the grinder body 13 and the grinder cover plate 15, respectively. One or more grinding balls 11 are used in each of the grinding zones 5. At least some portion of the interior grinding surface of the parallel grinder 12 can be the same as at least some portion of the interior pressing surface of the parallel press 20 and/or of the interior crushing surface of the parallel crusher 50. That is, at least one component is common to, and universal for, both the parallel grinder 12 and the parallel press 20 and/or the parallel crusher 50. With reference to FIGS. 4B, 4C and 4D, for example, the grinder body 13 of the parallel grinder 12 can be the same structural component as the press body 23 of the parallel press 20, and/or as the crusher body 53 of the parallel crusher 50. Additionally, the material-containing synthesis substrate 110 used in the parallel grinder 12 can also be a common component of, and universal for the parallel press 20 and/or the parallel crusher 50, thereby allowing for efficient parallel material transfer between these devices.

FIG. 4A represents catalysis materials being prepared or provided at each of four or more spatially discrete synthesis regions of a common substrate, each being defined by a synthesis surface of the substrate. As noted, the synthesis substrate can also be an integral component of the parallel grinder 12 (e.g., defining an end portion of the interior grinding surface), the parallel press 20 (e.g., defining an end portion of an interior pressing surface), and/or the parallel crusher 50 (e.g., defining an end portion of an interior crushing surface), preferably where the parallel crusher 50 has an integral primary sieve 58. Moreover, the synthesis substrate can further be a supporting substrate for various characterization approaches, as well as for various chemical and/or physical treatments. The particular embodiment depicted in FIG. 4A should not be considered limiting of the format for the synthesis substrate 110. Generally, the material-containing regions can be defined by any suitable physical barriers or structure (e.g., dimples, wells, vessels), and/or by chemical barriers (e.g., hydrophilic regions and/or hydrophobic spaces between regions.

FIGS. 3A, 3B and 3C also demonstrate this concept of the invention—showing that commonality of, and universality for components of the parallel mechanical treatment apparatus such as the parallel press 20 and/or parallel crusher 50 can be achieved with components for effecting chemical treatments and/or physical treatments (e.g., calcining) and/or characterization. Specifically, FIG. 3B depicts a plurality of catalysts 100 compacted (i.e., pressed) into pressed catalyst pellets 102, and supported for in situ further chemical and/or physical treatments, and/or for further characterization studies.

A particularly suitable format for effecting the aforementioned mechanical treatments can include a substrate, preferably an inert substrate having 96 or more wells in a microtiter plate format (e.g., 8×12 array with about 0.9 mm spacing center to center). The substrate can have at least partial universality with one or more of the aforedescribed protocols for parallel synthesis of catalysis materials, grinding, mixing, pressing, crushing, sieving and/or fractionating of the catalysis materials. If reaction screening can include parallel batch reactions, such a format can also be employed universally as a parallel batch reactor, for example, as taught in U.S. Ser. No. 09/619,416 filed Jul. 19, 2000 by VanErden et al.

Parallel Isostatic Press

As noted above, a parallel isostatic press can be used in connection with the present invention—as a stand alone parallel press, and/or as an integral subcomponent of a larger parallel treatment assembly, such as an integrated parallel pressing/crushing/sieving device (e.g., as shown and described in connection with FIGS. 3A through 3E) and/or an integrated device having at least one common universal structure (e.g., as shown and described in connection with FIGS. 4A through 4D).

Briefly, with reference to FIGS. 5A through 5D, a parallel isostatic press 320 can comprise a plurality, preferably four or more (or higher numbers, as generally described above) of spatially discrete pressing zones 330 defined at least partially by spatially discrete wells, dimples or depressions (e.g., shallow wells, preferably with rounded upper edges, as shown in FIGS. 5A through 5C, and/or deep wells, as shown in FIG. 5D), apertures or dimples formed in a press body 323. The press body can be a unitary member or alternatively, can comprise two or more integral pieces (not shown). Each of the plurality of pressing zones 330 are further defined by a one or more pressing membranes 340 that act as one or more pressing elements, and preferably, by a unitary pressing membrane 340 having a first membrane surface 341 and a second membrane surface 342. One or more pressure chambers, such as a common pressure chamber 350 (FIG. 5A), modular pressure chambers 350a, 350b, 350c (FIG. 5B), or separate individual pressure chambers 350a, 350b, 350c (FIG. 5C) (and indicated as 350 in FIG. 5D) is generally defined by an interior cavity surface of a pressure chamber body 352 and one or more pressing membranes, such as a unitary pressing membrane 340 (FIG. 5A), modular pressing membranes 340a, 340b, 340c (FIG. 5B), or separate individual pressing membranes 340a, 340b, 340c (FIG. 5C). The pressing membranes 340 can be of any suitable pressurizable materials, and is preferably a material having a substantial degree of elasticity. Exemplary materials for the one or more pressing membranes 340 can include butyl rubber or viton. As shown in FIG. 5A, the pressing membrane 340 is extended to be situated between, and to act as a gasket seal between the pressure chamber body 352 and the press body 323. Other sealing arrangements, such as separate independent gaskets 332 (FIGS. 5B and 5C) can also be employed.

In operation, referring to FIG. 5A, the pressure chamber 350 is filled with a fluid, preferably a liquid, through inlet line 354, and is pressurized from one or more pressure sources, such as a pump 356, such that a pressure is exerted on the second membrane surface 342 of the pressing membrane 340. Pressure can be sensed for example, using pressure sensor/optional detector (indicated as a circled "P" in the various figures. A plurality of spatially discrete regions of the first membrane surface 341 of the pressing membrane 340 contact the catalysis materials 100 situated in each of the spatially discrete pressing zones 330, to simultaneously press the catalysis materials 100. Similar operational aspects are provided with respect to the modular pressure chambers 350a, 350b, 350c (FIG. 5B) and/or individual pressure chambers 350a, 350b, 350c (FIG. 5C), except that increased operational pressures are generally attainable therewith. Moreover, separate pressure control can be effected in each of the pressure chambers (e.g., as shown for the modular pressure chambers, FIG. 5B, through separate and independent pressure lines 354a, 354b, 354c. Such variation allows, as one example, an apparatus and a protocol for evaluating various pressing conditions. A single, common pressure control valve can also be used in connection with the modular pressure chambers and/or individual pressure chambers (e.g., as shown for the individual pressure chambers, FIG. 5C, through a common pressure line 354.

Parallel Roller Press

The parallel press can be a parallel roller press comprising four or more pressing zones, with each zone comprising or being defined by one or more roller presses. The parallel roller press can be a stand-alone device, or can be part of an integrated multi-functional device.

Referring now to FIGS. 7A through 7D, each of the roller presses 700 of the parallel roller press can comprise at least two rollers 710a, 710b in peripheral contact with each other. The rollers 710a, 710b can be driven by roller shafts 720a, 720b, respectively. The roller shafts 720a, 720b can each have a first end 721a, 721b and opposing second ends 722a, 722b, and can comprise a portion (e.g., ends or mid-sections thereof) that are themselves the rollers 710a, 710b, or that are drivingly coupled to rollers 710a, 710b. The particular arrangement of roller shafts 720a, 720b is not critical; the roller shafts 720a, 720b can extend on first and second opposing sides 704, 706 of roller housing 705, or alternatively, can be arranged to extend on the same side of the roller housing 705. Materials, such as catalysis materials, can be fed into the roller press 700 through inlet funnel 730. The inlet funnel 730 preferably comprises a first upper tapered section 732 having an open end 733 and a second lower substantially cylindrical section 734. The inlet funnel 730 can be a unitary funnel, or a two-piece funnel, and can be supported, directly or indirectly, on or by feed plate 736, which can be releasably attached to the roller housing 705, for example, using fasteners 738. As shown in FIG. 7C, the lower end 735 of the lower section 734 of inlet funnel 730 can be in substantial sealing contact with the rollers 710a, 710b, with the seal being maintained by the action of funnel spring 740. The inlet funnel can be of suitable volumetric (or weight) capacity for the application of interest. For catalysis materials for use in connection with combinatorial heterogeneous catalysis research, for example, the inlet funnel 730 can be sized to accommodate up to about 100 g, preferably up to about 10 g, and in some embodiments, up to about 1 g of catalysis materials.

Materials are pressed between the rollers 710a, 710b under a compressive force maintained between the rollers 710a, 710b by roller bushings 750a, 750b (FIG. 7D) which are in a reduced-friction contact with a substantially adjacent portion of the roller shafts 720a, 720b. A compressive force can be applied to one or both of the roller bushings 750a, 750b by one or more roller springs 760, which is generally supported by roller housing 705, and which, as shown, has a first end 761 in contact with roller bushing 750b and a second opposing end 762 in contact against roller-spring preload adjustment screw 764. The amount of force applied to rollers 710a, 710b by roller spring 760 is not critical to the invention, and can generally vary depending on the type of materials being pressed, and the desired characteristics of the pressed materials, and is typically suitable for agglomerating smaller particles into a larger compressed mass. In one embodiment, the rollers 710a, 710b can have a contact stress of about 100,000 psi due to the spring preload. After passing through the rollers 710a, 710b, the materials can be discharged from the roller press 700 through exit passage (FIG. 7C). As shown in FIGS. 7A through 7D, the pressing zone is generally defined by an interior surface comprising an interior surface of the lower section 734' of the inlet funnel 730, the outer surface of rollers 710a, 710b (as they roll in contact with the materials), and an interior surface 772 of the outlet passage 770, which, as shown, can be integrally formed within the roller housing 705.

Parallel Finger-Die Crushing/Sieving Device

As noted above, a parallel finger-die type crushing/sieving device (or parallel crushing/sieving/fractionating device) can be used in connection with the present invention—as a stand-alone device, but preferably as an integral subcomponent of a larger parallel treatment assembly, such as an integrated parallel pressing/crushing/sieving/fractionating device (e.g., as shown and described in connection with FIGS. 3A through 3E) and/or an integrated device having at least one common universal structure (e.g., as shown and described in connection with FIGS. 4A through 4D).

Briefly, with reference to FIGS. 6A through 6D, a finger-die parallel crushing/sieving device 450 comprises a plurality, and preferably four or more (or higher numbers, as generally described herein) crushing zones 470. Each of the four or more crushing zones 470 are defined by an interior crushing surface. The interior crushing surface can be defined for each of the crushing zones 470 by side walls 452 of apertures formed in crusher body 453, by a spatially discrete region of an upper surface 427 of a unitary lower die 426, by a bottom surface 429 of an upper die 428, and by exposed surfaces of upper die fingers 430. The crusher body 453 and lower die 426 can be sealed by one or more seals, such as a unitary gasket 432. The lower die 426 can be a unitary lower die (as shown) or can be a plurality of, and preferably four or more separate lower dies (not shown). A unitary lower die (or a modular lower die) can comprise a plurality and preferably four or more spatially discrete die regions, with each of the regions (or each of the individual lower dies, in embodiments having separate individual lower dies) comprising a number of apertures 455, and preferably ten or more apertures, twenty-five or more apertures, forty or more apertures or one-hundred or more apertures. Significantly, the number of apertures 455, size of the apertures 455 and spatial arrangement of the apertures 455 of the lower die 426 preferably correspond to the number, size and spatial arrangement, respectively, of the die fingers 430 of the upper die 428. Alignment posts 410 corresponding to alignment apertures 412 can be used to align the upper dies 428 and lower dies 426, and in particular, the die fingers 430 and the die apertures 455 thereof. Materials 100, such as catalysis materials can be situated in each of the crushing zones 470. In operation, a substantially vertical, preferably reciprocating motive force is applied to upper die plate 462 and translating to each of the upper dies 428, so that die fingers 430 can be repeatedly extended downward through the die apertures 455 of the lower die 426, thereby crushing at least some portion of the materials 100, and integrally therewith, sieving some of the crushed portion. Hence, the lower die 426 operates integrally as a crusher and a siever of materials 100. After the downward extension, the die fingers 430 can be retracted upward back into the crushing zone 470, allowing additional larger chunks of materials to fall into place over the apertures 455 of the lower die. Agitation, such as orbital agitation can be applied to the parallel crusher/siever 450 to facilitate such redistribution of materials 100. The die fingers 430 are then repeatedly extended downward and retracted upward to integrally crush and sieve each of the plurality, and preferably each of the four or more materials simultaneously in the various crushing regions.

Figure 6A:
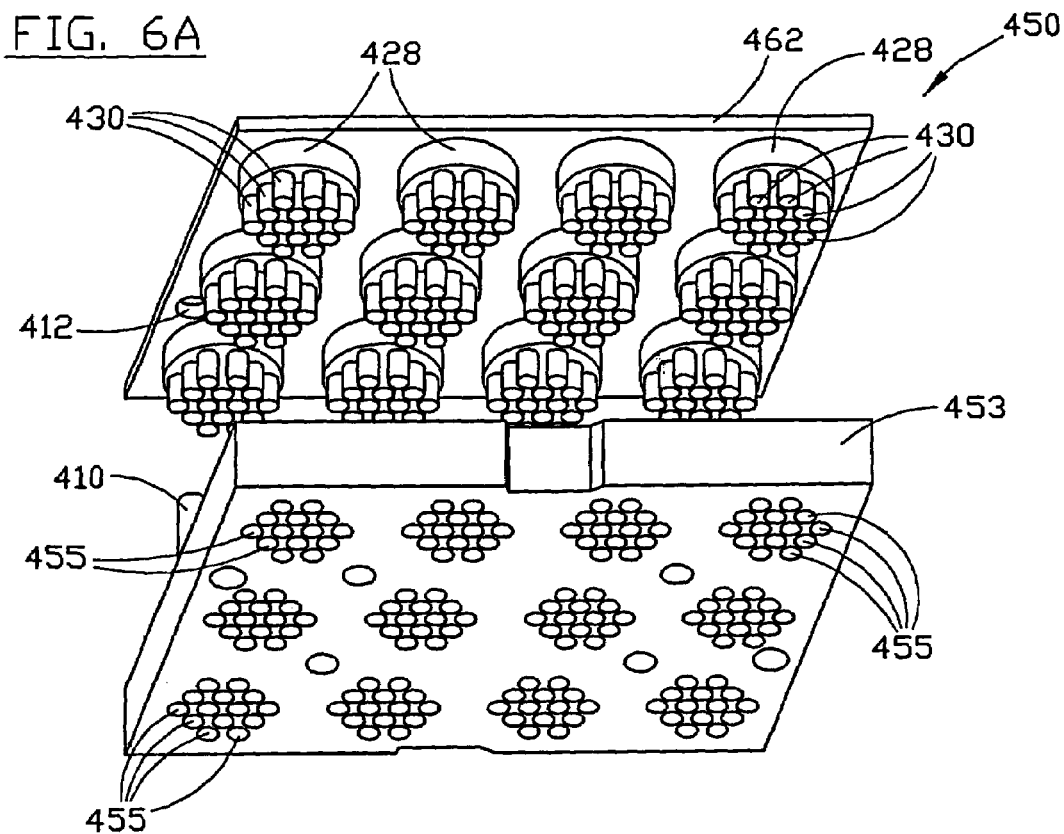
FIG. 6A through FIG. 6D are schematic perspective views (FIGS. 6A, 6C and 6D) or cross-sectional detail views (FIG. 6B) of a parallel finger-die crushing and sieving device (FIGS. 6A and 6B), and of an integrated parallel finger-die crushing/sieving/fractionating device (FIG. 6C, showing a bottom perspective view, and FIG. 6D, showing a top perspective view).
Figure 6B:
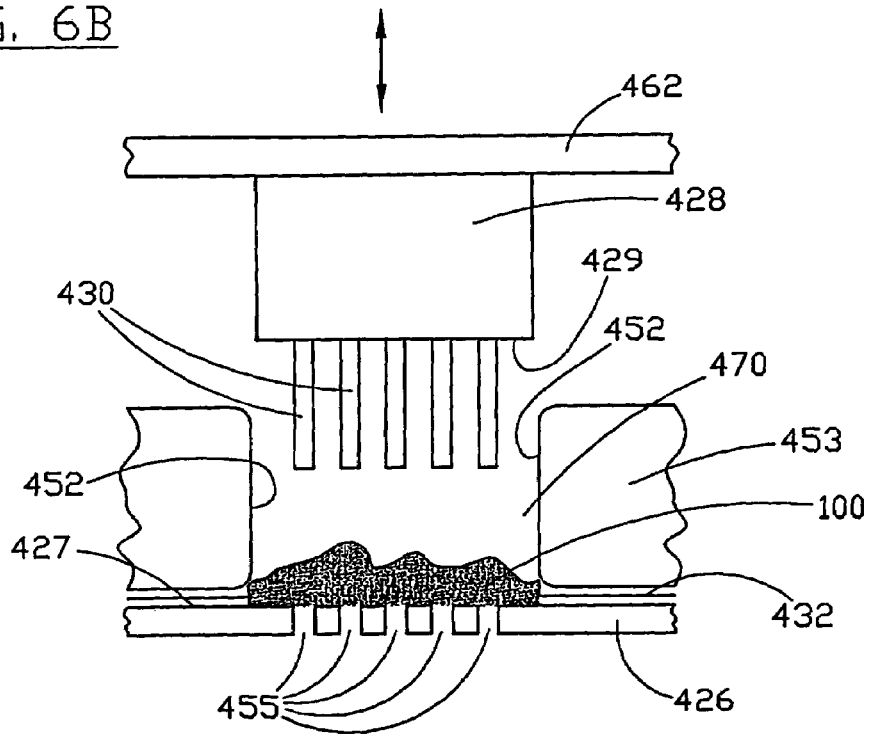
Figure 6C:
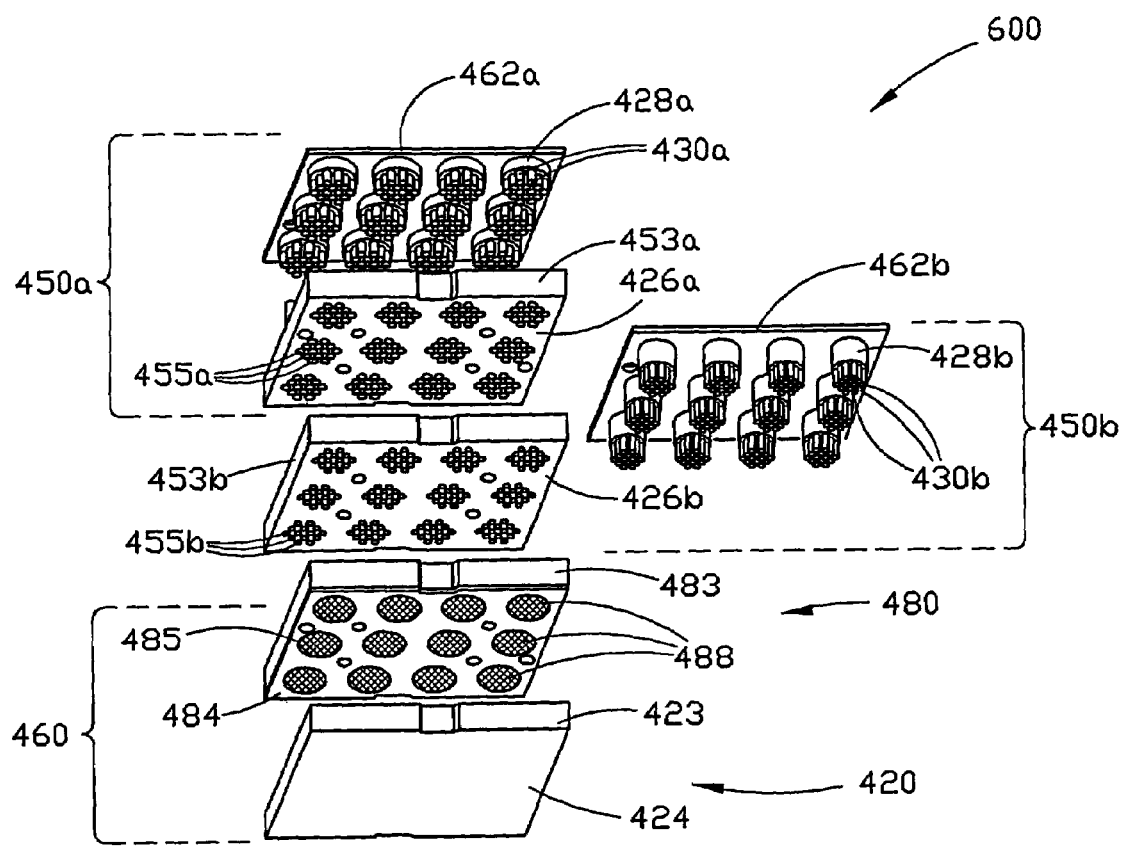
Figure 6D:
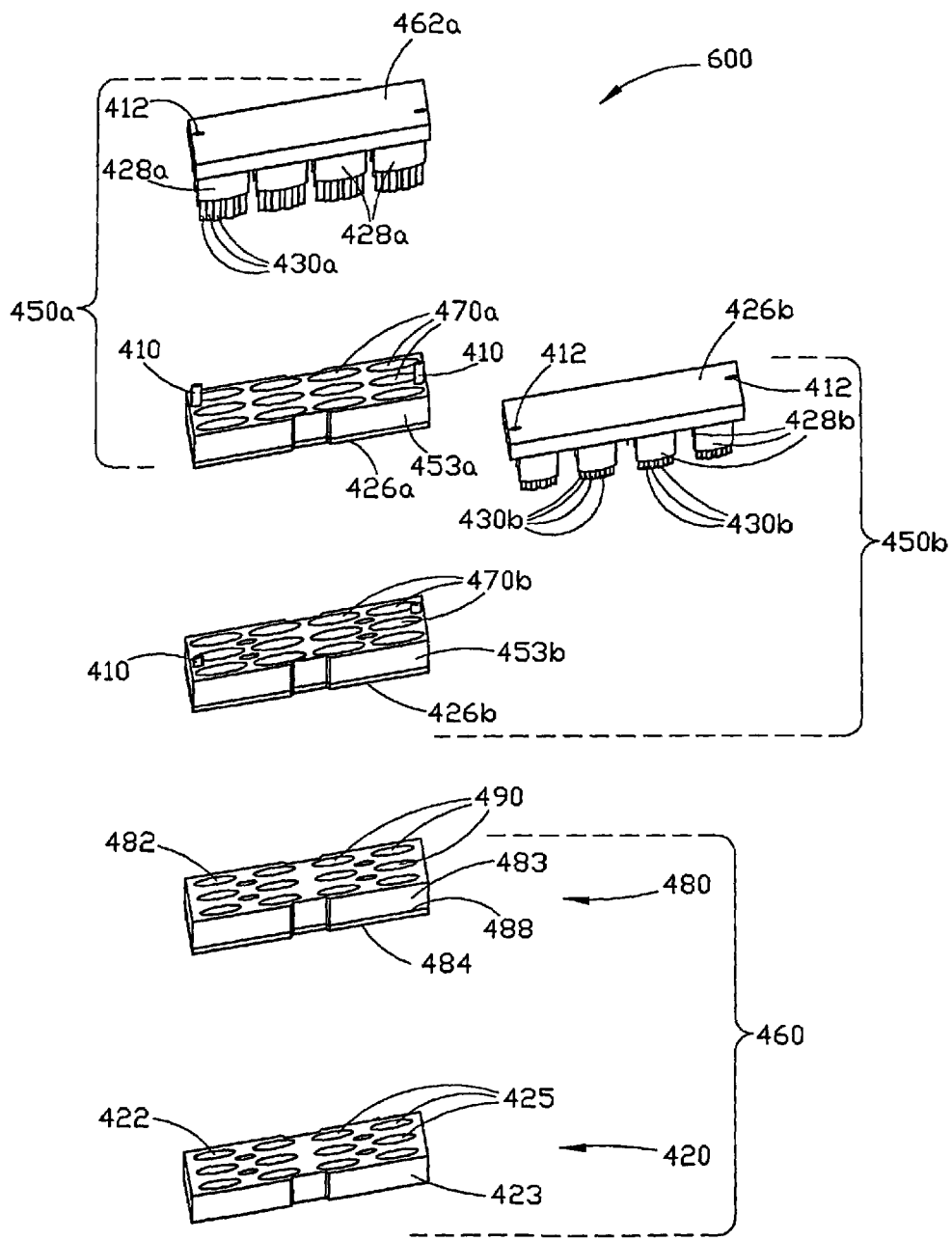

Referring further to FIGS. 6C and 6D, a two-stage parallel finger-die crushing/sieving/fractionating device 600 can be employed based on the single-stage parallel finger-die crusher 450 shown and described in connection with FIGS. 6A and 6B. As shown, the integrated device 480 comprises a first stage parallel finger-die crusher 450a, a second stage parallel finger-die crusher 450b, and a parallel fractionater 460.

Each of the first stage and second stage parallel finger-die crushers 450a, 450b can comprise a plurality of, and preferably four or more crushing zones 470a, 470b, with each such crushing zone having associated therewith an upper die 428 and a lower die 426, substantially as described in connection with FIGS. 6A and 6B. The first stage parallel finger-die crusher 450a can be a coarse crushing stage, having die fingers 430a of the upper dies 428a and associated apertures 455a of the lower dies 426a sized for coarse crushing of materials 100 to form coarse-sieved particles. The second stage parallel finger-die crusher 450b can be a medium or fine crushing stage, having die fingers 430b of the upper dies 428b and associated apertures 455b of the lower dies 426b sized for medium or fine crushing of the coarse-sieved materials, to form medium-sieved or fine-sieved materials. In operation, the first-stage crushing of the plurality of materials, preferably four or more materials, is effected such that each of the coarse-crushed and sieved materials are crushed and pushed through the first-stage apertures 455a of the lower die 426a by the associated first-stage die fingers 430a. The crushing may occur intermittently, with repeated impact of the die fingers 430a against the catalysis material 100 in combination with agitation to facilitate sieving through the first-stage apertures 455a. The first stage die fingers 430a may or may not penetrate the first-stage apertures 455a, or may only penetrate the apertures 455a as a clearing stroke after substantially all of the coarse-crushed materials have been sieved through the apertures 455a. In any event, the coarse-crushed materials are collected into recesses formed by the integral crusher body 453b and lower die plate 426b of the second stage crusher 450b—generally including the lower portion of the crushing zone 470b of the second stage parallel finger-die crusher 450b. After collection of the coarse-crushed and sieved materials, the upper die plate 462b of the second stage crusher 450b and the upper dies 428b associated therewith can be positioned over the integral crusher body 453b and lower die plate 426b, for medium or fine second stage crushing and sieving therein to form the medium-crushed and sieved or fine-crushed and sieved materials. Additional crushing stages (not shown) can also be employed.

The parallel fractionater 460 can comprise a parallel sieving device 480 and a parallel fines collector 420. The parallel sieve 480 can comprise a sieve body 483, that comprises a plurality of, and preferably four or more spatially discrete apertures corresponding in spatial arrangement to the plurality of, and preferably four or more crushing zones of the second stage parallel crusher 450b. Each of the four or more apertures of the sieve body 483 have an inlet end adapted to receive medium-crushed and sieved, or fine-crushed and sieved material passing though the second stage apertures 455b of the lower die 426b of the second stage parallel crusher 450b, and an opposing outlet end. A plurality of sieving zones 490 (e.g., sieving cavities) are defined by walls 482 of sieve body 483. The parallel sieve 480 also comprises one or more supplemental sieves 488 (e.g., tertiary sieves, considering the apertures 455a, 455b of the lower dies 426a, 426b to be coarse sieves and medium/fine sieves of the first and second stage crushers 450a, 450b, respectively), held in place for example by a bottom 484 of the sieve 480, comprising a plurality of apertures 485. The one or more supplementary sieves are preferably situated substantially at the outlet end of each of the four or more apertures of the sieve body 483. The one or more supplemental sieves can be individual, separate sieves, modular sieves having two or more spatially discrete sieving regions, and/or a unitary sieve having two or more, preferably four or more spatially discrete sieving regions, and in any case, are adapted to simultaneously sieve each of the plurality of, and preferably four or more medium-crushed and sieved or fine-crushed and sieved materials, such that for each of such materials, smaller supplementally-sieved (e.g., tertiary-sieved) particles (e.g., fines) pass through the supplementary sieve 483, whereas larger particles are retained by the sieve 483.

Additional parallel sieves (not shown) can likewise be employed, depending on the number of desired fractions. Some of the catalysis material particles are small enough such that they fall through the sieve 488, and can thereby be allowed to fall into a plurality of collection cavities 425 defined by walls 422 of a fines collector body 423 of the parallel fines collector 420. The parallel fines collector 420 further comprises a bottom 424. The collected smaller particles (e.g., fines) may be repressed, recrushed or reground, and resieved. The sieving units may generally also include vibrational agitation to help fractionate the catalyst particles/powder. Other motive forces, such as pneumatic fluid forces, are likewise contemplated to help move catalyst particles through the various sieves.

In a preferred embodiment, in which the two-stage parallel finger-die crushing/sieving/fractionating device 600 is applied to preparation of catalysis materials, the first coarse-stage crusher 450a can have die fingers 430a and associated apertures 455a with a diameter of about 2.5 mm to prepare first-stage crushed and sieved materials with a particle size of about 2.5 mm or less. A second, medium-stage crusher 450b can have die fingers 430b and associated apertures 455b with a diameter of about 0.8 mm to prepare second-stage crushed and sieved materials with a particle size of about 0.8 mm or less. Fines are removed from the second-stage crushed and sieved materials using parallel fractionator 480 having a unitary screen 488 with a mesh size that passes particles having a diameter of less than about 0.5 mm, while retaining particles having a diameter of 0.5 mm or more, such that a primary fraction having particles sizes ranging from about 0.5 mm to about 0.8 mm are provided in the parallel siever 480. Particles having a diameter of less than about 0.5 mm are collected in collection cavities 425 of parallel collector 420.

Generally, the finger-die press can be advantageously used for many materials (within mechanical design limits of the die fingers), and for many such applications, can result in a higher yield of fractionated materials.

Libraries of Catalysis Materials for Use in Combinatorial Catalysis Research

The present invention can be used in connection with various types of catalysis materials, and various types of catalysis platforms. Generally, catalysts can include metals, metal oxides, metal salts, and salts of metal oxides. Catalyst platforms can be libraries of catalysis materials that have common or related chemical (molecular) composition or structure. Exemplary catalyst platforms include supported or bulk mixed metal oxides (MMO's), noble metals (NM), noble-metal/transition metal (NM/TM), noble-metal/base metal (NM/BM) or oxides thereof, polyoxometallates (POM's), and molecular sieves (e.g., zeolites and other related, microporous and mesoporous materials), among others. The members of a catalyst platform can be presynthesized, and available in library format as source materials, which can in application, be daughtered for use in synthesis protocols to prepare the arrays of the present inventions. The members of a catalyst platform can also be synthesized in situ for use in connection with the present invention. The libraries can also include libraries of mixed platforms, such as functionally-defined libraries such as disclosed in co-owned, co-pending U.S. patent application, Ser. No. 09/901,858, published as U.S. 2002/0042104, entitled "Methods for Analysis of Heterogeneous Catalysts in a Multi-Variable Screening Reactor" filed on Jul. 9, 2001 by Hagemeyer et al., such patent application being hereby incorporated by reference in its entirety for all purposes.

A library of catalysis materials, and/or a synthesis or screening protocol for such a library, can be characterized as (and in general, should be considered generic to, unless specifically recited otherwise) a primary screen, a secondary screen, a tertiary screen, a quaternary screen, and/or a higher-order screen. The library and/or synthesis or screening protocols can likewise be characterized as (and in general, should be considered generic to) an initial library/screen directed toward initial identification of hits or leads, or a related, subsequent focus library/screen. See, for example, as previously described in U.S. Ser. No. 09/518,794 filed Mar. 3, 2000 by Bergh et al. The number of catalysis materials in the library or array is preferably four or more, more preferably eight or more, sixteen or more, twenty-four or more, forty-eight or more, ninety-six or more, two-hundred or more, four hundred or more, one thousand or more, four thousand or more, ten thousand or more, or in some embodiments, 96*N, where N ranges from 1 to about 20, and preferably from 1 to about 5.

In preferred embodiments, the plurality of catalysts or catalyst precursors (e.g., including catalyst supports) of the library are different from each other with respect to composition and/or concentration. The compositional space of the library can typically comprise four or more diverse compositions having one or more common elements at various concentrations or stoichiometries (a unitary library), preferably two or more common elements at various concentrations or stoichiometries (a binary library) more preferably three or more common elements at various concentrations or stoichiometries (a ternary library), or a higher-order library (e.g., a quaternary library). See U.S. Pat. No. 5,985,356 to Schultz et al., and U.S. patent application Ser. No. 09/156,827 filed Sep. 18, 1998 by Giaquinta et al. In a ternary library comprising elements A, B, and C, for example, each of A, B and C can range from 0% to 100% within the ternary library at various stoichiometric increments (e.g., at 10% increments). The library can also include one or more standard compositions present at a plurality of test regions (e.g., reaction vessels or reaction sites) of an array. In some embodiments, a standard composition is preferably present at three or more test regions, four or more test regions, six or more test regions, or eight or more test regions.

The library of catalysis materials can also be developed and differentiated with respect to process conditions. Generally, process conditions refers, inclusively, to (i.e., is intended as being generic to) synthesis protocols (e.g., precipitation, impregnation, spray drying, etc.), synthesis conditions within a particular synthesis protocol, pretreatment protocols (e.g., physical pretreatments such as heating or calcining, mechanical pretreatments such as compaction, grinding, sieving, and/or chemical pretreatments such as reduction (e.g., by H2, C2H4, etc.), activation (e.g., by C2H4), partial oxidation, etc., pretreatment conditions within a particular pretreatment protocol, reaction conditions (e.g., selected from the group consisting of temperature, pressure, space velocity and contact time), regeneration conditions (e.g., post-reaction treatments prior to reuse), and any other catalytically significant process variables prior to, during, or subsequent to catalytic (reaction-based) screening of the candidate catalyst material for a particular reaction (or reactions) of interest.

Variations in process conditions can, in general, be simultaneous (i.e., parallel variation in conditions), serial, or semi-parallel (i.e., serial with respect to a parallel subset). Reaction conditions for synthesis can be varied within elements of an array, or between different arrays. See for example, U.S. Pat. No. 6,004,617 to Schultz et al. Reaction conditions during screening can also be varied between different arrays and/or within elements of an array. For example, screening reaction conditions can be simultaneously varied using a multi-variable optimization reactor (MVO) such as that described in U.S. Ser. No. 60/185,566 filed Mar. 7, 2000 by Bergh et al., U.S. Ser. No. 09/801,390 filed Mar. 7, 2001 by Bergh et al., and U.S. Ser. No. 09/801,389 filed Mar. 7, 2001 by Bergh et al. Catalytic performance can be characterized by any suitable performance-indicating parameter. Conversion and selectivity for a particular reaction of interest are particularly preferred. See, for example, U.S. Ser. No. 09/518,794 filed Mar. 3, 2000 by Bergh et al.; see also U.S. Ser. No. 09/093,870 filed Jun. 9, 1998 by Guan et al.

Combinatorial Mechanical Pretreatment Protocols

The mechanical pretreatement protocols described herein, including especially for example, one or more of the steps of grinding, mixing, pressing, crushing, sieving and/or fractionating, variously repeated as described, and variously interspersed with one or more additional chemical and/or physical pretreatment steps, can have substantial impact on material performance such as catalysis material performance.

As such, one aspect of the invention relates to a method for systematically varying and exploring the mechanical treatment process conditions to which a library of materials, such as catalysis materials, are exposed. Hence for example, the aforementioned parallel methods of grinding, mixing, pressing, crushing, sieving, and/or fractionating can each be explored with respect to variations in one or more operational parameters associated therewith. For example, parallel grinding can be effected with different types, sizes, amounts or conditions (e.g. dry versus wet, and if wet, variations in types of grinding solvents) of grinding media in each of the four or more channels of the parallel grinder. Additionally or alternatively, parallel pressing can be effected with variations in pressing pressures, varying press-types (e.g., roller vs. die press) or variations in die shapes (e.g., for die presses) associated with each of four or more channels of the parallel press. Considered cumulatively, the number of repeated cycles of grinding and pressing (optionally together with or without chemical and/or physical treatments such as calcining) can be varied between the four or more different catalysis materials. Additionally or alternatively, parallel crushing and sieving can be effected to vary the crushing media and/or preferably, to vary the size of the fractioned particles being screened (i.e., different fractions of each of the four or more materials can be used in separate reaction-based screenings, to simultaneously evaluate differences in particle size in each of four or more reaction zones). Evaluation of particle size variation can be especially helpful, alone or in combination with variations in linear reactant velocity, to determine diffusion limitations (e.g., pore diffusion, alone or in combination with film diffusion), for example, with respect to studies of intrinsic activity or kinetic activity. Other variations will be apparent to those of skill in the art.

The following examples illustrate the principles and advantages of the invention.

EXAMPLES

Example 1

Effect of Pelletizing, Crushing, Sieving on Catalyst Performance

The catalytic performance of mixed metal oxide catalysts was evaluated using catalyst candidates subjected to various pretreatment conditions. A batch of catalyst was prepared by solvent evaporation. One portion of the batch was finely ground and pressed into a pellet. The other portion was lightly ground to a powder. Both samples were subsequently calcined under identical conditions. The pelletized sample was then crushed and sieved. Both samples were then screened in a parallel flow reactor. The yield obtained from the ground, pressed (i.e., pelletized), crushed and sieved sample was 2.8 times higher than the unpelletized sample.

In light of the detailed description of the invention and the examples presented above, it can be appreciated that the several objects of the invention are achieved.

The explanations and illustrations presented herein are intended to acquaint others skilled in the art with the invention, its principles, and its practical application. Those skilled in the art may adapt and apply the invention in its numerous forms, as may be best suited to the requirements of a particular use. Accordingly, the specific embodiments of the present invention as set forth are not intended as being exhaustive or limiting of the invention.

We claim:

1. An apparatus for parallel grinding of materials, the apparatus comprising
    four or more spatially discrete apertures or wells arranged in a generally planar array, each of the four or more apertures or wells defining a grinding zone having an interior grinding surface,
    grinding balls adapted for impacting motion within the four or more grinding zones and being adapted for grinding materials residing in one of the four or more grinding zones,
    one or more primary sieves defining at least a portion of the interior grinding surface for each of the four or more grinding zones, the one or more primary sieves being adapted to simultaneously sieve each of the four or more materials as they are being ground, such that for each of the four or more materials, smaller, primary-sieved particles pass through the primary sieve whereas larger, unsieved particles are retained in the grinding zone for further grinding, and
    wherein the grinding zones are in a grinder body and said apertures or wells have vertical longitudinal axes and extend generally vertically down from an upper surface of the grinder body.

2. The apparatus of claim 1, further comprising a sieve body comprising four or more spatially discrete apertures corresponding in spatial arrangement to the four or more apertures or wells of the grinder body, each of the four or more apertures of the sieve body having an inlet end adapted to receive primary-sieved particles passing through the primary sieve, and an opposing outlet end.

3. The apparatus of claim 1 wherein the one or more primary sieves comprise four or more separate, individual primary sieves.

4. The apparatus of claim 1 further comprising a cover plate on said grinder body extending over said apertures or wells.

5. An apparatus for parallel grinding of materials, the apparatus comprising
    four or more spatially discrete apertures or wells, each of the four or more apertures or wells defining a grinding zone having an interior grinding surface,
    grinding balls adapted for impacting motion within the four or more grinding zones and being adapted for grinding materials residing in one of the four or more grinding zones,
    one or more primary sieves defining at least a portion of the interior grinding surface for each of the four or more grinding zones, the one or more primary sieves being adapted to simultaneously sieve each of the four or more materials as they are being ground, such that for each of the four or more materials, smaller, primary-sieved particles pass through the primary sieve whereas larger, unsieved particles are retained in the grinding zone for further grinding,
    a sieve body comprising four or more spatially discrete apertures corresponding in spatial arrangement to the four or more apertures or wells of the grinder body, each of the four or more apertures of the sieve body having an inlet end adapted to receive primary-sieved particles passing through the primary sieve, and an opposing outlet end, and
    one or more second secondary sieves situated substantially at the outlet end of each of the four or more apertures of the sieve body, the one or more secondary sieves being adapted to simultaneously sieve the primary-sieved particles of each of the four or more materials, such that for each of the four or more materials, smaller secondary-sieved particles pass through the secondary sieve whereas larger primary-sieved particles are retained by the secondary sieve,
    the one or more primary sieves having a mesh size that is larger than a mesh size of the one or more secondary sieves, such that primary fractions of each of the four or more materials can be formed in the apparatus, the primary fractions having a particle size distribution substantially ranging from about the mesh size of the secondary sieve to about the mesh size of the primary sieve.

6. The apparatus of claim 5 wherein the one or more secondary sieves comprise four or more separate, individual secondary sieves.

7. The apparatus of claim 5 wherein the one or more secondary sieves comprise a unitary secondary sieve having at least two discrete sieving regions.

8. The apparatus of claim 5 wherein the one or more secondary sieves comprise a unitary secondary sieve having four or more discrete sieving regions.

9. An apparatus for parallel grinding of materials, the apparatus comprising
- four or more spatially discrete apertures or wells, each of the four or more apertures or wells defining a grinding zone having an interior grinding surface,
- grinding balls adapted for impacting motion within the four or more grinding zones and being adapted for grinding materials residing in one of the four or more grinding zones,
- one or more primary sieves defining at least a portion of the interior grinding surface for each of the four or more grinding zones, the one or more primary sieves being adapted to simultaneously sieve each of the four or more materials as they are being ground, such that for each of the four or more materials, smaller, primary-sieved particles pass through the primary sieve whereas larger, unsieved particles are retained in the grinding zone for further grinding, and
- wherein the one or more primary sieves comprise a unitary primary sieve having at least two discrete sieving regions.

10. An apparatus for parallel grinding of materials, the apparatus comprising
- four or more spatially discrete apertures or wells, each of the four or more apertures or wells defining a grinding zone having an interior grinding surface,
- grinding balls adapted for impacting motion within the four or more grinding zones and being adapted for grinding materials residing in one of the four or more grinding zones,
- one or more primary sieves defining at least a portion of the interior grinding surface for each of the four or more grinding zones, the one or more primary sieves being adapted to simultaneously sieve each of the four or more materials as they are being ground, such that for each of the four or more materials, smaller, primary-sieved particles pass through the primary sieve whereas larger, unsieved particles are retained in the grinding zone for further grinding, and
- wherein the one or more primary sieves comprise a unitary primary sieve having four or more discrete sieving regions.

11. An apparatus for parallel crushing of materials, the apparatus comprising
- a crusher body comprising four or more spatially discrete apertures or wells arranged in a generally planar array, each of the four or more apertures or wells defining a crushing zone having an interior crushing surface,
- milling balls within each of the four or more crushing zones, the milling balls being adapted for crushing materials residing in the crushing zone,
- one or more primary sieves defining at least a portion of the interior crushing surface for each of the four or more crushing zones, the one or more primary sieves being adapted to simultaneously sieve each of the four or more materials as they are being crushed or intermittently between repeated crushing steps, such that for each of the four or more materials, smaller, primary-sieved particles pass through the primary sieve whereas larger, unsieved particles are retained in the crushing zone for further crushing, and
- wherein said apertures or wells have vertical longitudinal axes and extend generally vertically down from an upper surface of the crusher body.

12. The apparatus of claim 11 further comprising a substrate on said crusher body extending over said apertures or wells.

* * * * *